US008618251B1

(12) United States Patent
Ravetch et al.

(10) Patent No.: US 8,618,251 B1
(45) Date of Patent: Dec. 31, 2013

(54) FC MUTANTS

(75) Inventors: Jeffrey V. Ravetch, New York, NY (US); Rene G. Ott, Vienna (AT)

(73) Assignee: The Rockefeller University, New York, NY (US)

( * ) Notice: Subject to any disclaimer, the term of this patent is extended or adjusted under 35 U.S.C. 154(b) by 406 days.

(21) Appl. No.: 12/942,824

(22) Filed: Nov. 9, 2010

Related U.S. Application Data

(60) Provisional application No. 61/259,457, filed on Nov. 9, 2009.

(51) Int. Cl.
*C07K 1/00* (2006.01)
*C07K 16/00* (2006.01)
*C12P 21/08* (2006.01)
*C07K 17/00* (2006.01)

(52) U.S. Cl.
USPC ............... 530/350; 530/387.1; 530/387.3; 530/388.1; 530/391.1

(58) Field of Classification Search
None
See application file for complete search history.

(56) References Cited

U.S. PATENT DOCUMENTS

| | | | |
|---|---|---|---|
| 6,737,056 B1 * | 5/2004 | Presta | 424/133.1 |
| 7,317,091 B2 | 1/2008 | Lazar et al. | |
| 2004/0110226 A1 * | 6/2004 | Lazar et al. | 435/7.1 |

* cited by examiner

*Primary Examiner* — Chun Dahle
(74) *Attorney, Agent, or Firm* — Fox Rothschild LLP; Gerard P. Norton; Jianming J. Hao

(57) ABSTRACT

The present invention provides reagents, methods and systems for predicting the inhibitory activity of an antibody or variant thereof comprising: determining a binding affinity of the antibody or variant thereof to a Fc activating receptor; determining a binding affinity of the antibody or variant thereof to a Fc inhibitory receptor, and calculating the ratio of said activating binding affinity to said inhibitory binding affinity (A/I ratio), wherein the magnitude of said ratio is less than one (1).

11 Claims, 8 Drawing Sheets

SPR analysis of hFc1-variants

| code | hRIIA$^{131H}$ | hRIIA$^{131R}$ | hRIIB | hRIIIA$^{158F}$ | C1q |
|---|---|---|---|---|---|
| wt | 4.3 E-06 | 4.8 E-06 | 2.4 E-05 | 3.5 E-06 | 2.9 E-07 |
| IEAL | 4.8 E-06 | 3.7 E-07 | 3.2 E-06 | 4.9 E-07 | 1.4 E-07 |
| ALEV | 7.2 E-06 | 7.8 E-07 | 6.1 E-06 | 3.4 E-06 | n.d. |
| LLLFET | 3.4 E-06 | 5.2 E-07 | 7.9 E-07 | 3.1 E-06 | n.d. |
| NREIT | 2.9 E-06 | 5.8 E-07 | 4.0 E-06 | 5.2 E-07 | 1.2 E-07 |

$K_D$ (M)
n.d. not done

FIG. 1

```
                              SEQUENCE LISTING

<160> NUMBER OF SEQ ID NOS: 32

<210> SEQ ID NO 1
<211> LENGTH: 447
<212> TYPE: PRT
<213> ORGANISM: Homo sapiens
<220> FEATURE:
<221> NAME/KEY: misc_feature
<222> LOCATION: (1)..(117)
<223> OTHER INFORMATION: Xaa can be any naturally occurring amino acid

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

-continued

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 2
<211> LENGTH: 27
<212> TYPE: DNA
<213> ORGANISM: Artificial Sequence
<220> FEATURE:
<223> OTHER INFORMATION: DNA primer sequence

<400> SEQUENCE: 2
aattgaattc gcctccacca agggccc                                    27

<210> SEQ ID NO 3
<211> LENGTH: 30
<212> TYPE: DNA
<213> ORGANISM: Artificial Sequence
<220> FEATURE:
<223> OTHER INFORMATION: DNA primer sequence

<400> SEQUENCE: 3
aattctcgag tcatttaccc ggagacaggg                                 30

<210> SEQ ID NO 4
<211> LENGTH: 50
<212> TYPE: DNA
<213> ORGANISM: Artificial Sequence
<220> FEATURE:
<223> OTHER INFORMATION: DNA primer sequence

<400> SEQUENCE: 4
atctgtacga cgatgacgat aaggtaccag gatccagtgt ggtggaattc            50

<210> SEQ ID NO 5
<211> LENGTH: 50
<212> TYPE: DNA
<213> ORGANISM: Artificial Sequence
<220> FEATURE:
<223> OTHER INFORMATION: DNA primer sequence

<400> SEQUENCE: 5
agagggttag ggataggctt accttcgaag ggccctctag actcgagtca            50

<210> SEQ ID NO 6

```
<211> LENGTH: 19
<212> TYPE: DNA
<213> ORGANISM: Artificial Sequence
<220> FEATURE:
<223> OTHER INFORMATION: DNA primer sequence

<400> SEQUENCE: 6
caccaagggc ccatcggtc                                                19

<210> SEQ ID NO 7
<211> LENGTH: 30
<212> TYPE: DNA
<213> ORGANISM: Artificial Sequence
<220> FEATURE:
<223> OTHER INFORMATION: DNA primer sequence

<400> SEQUENCE: 7
aattgaattc tcatttaccc ggagacaggg                                    30

<210> SEQ ID NO 8
<211> LENGTH: 182
<212> TYPE: PRT
<213> ORGANISM: Artificial Sequence
<220> FEATURE:
<223> OTHER INFORMATION: Fragment of the FC variant of an IgG anitbody

<400> SEQUENCE: 8

Ile Glu Pro Lys Ser Cys Asp Lys Thr His Thr Cys Pro Pro Cys Pro
  1               5                  10                  15

Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45

Val Val Asp Val Ser His Glu Asp Pro Glu Val Lys Phe Asn Trp Tyr
     50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Glu
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Ala Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Leu
            180

<210> SEQ ID NO 9
<211> LENGTH: 108
<212> TYPE: PRT
<213> ORGANISM: Artificial Sequence
<220> FEATURE:
<223> OTHER INFORMATION: Fragment of the FC variant of an IgG anitbody

<400> SEQUENCE: 9

Leu Lys Asp Thr Leu Leu Ile Ser Arg Thr Pro Glu Val Thr Cys Val
  1               5                  10                  15
```

-continued

```
Val Val Asp Leu Ser His Glu Asp Pro Glu Val Lys Phe Asn Trp Phe
         20                  25                  30

Val Asp Gly Glu Glu Val His Asn Ala Lys Thr Lys Pro Arg Glu Glu
         35                  40                  45

Gln Tyr Asn Ser Thr Tyr Arg Val Val Ser Val Leu Thr Val Leu His
 50                  55                  60

Gln Asp Trp Leu Asn Gly Lys Glu Tyr Lys Cys Lys Val Ser Asn Lys
 65                  70                  75                  80

Ala Leu Pro Ala Pro Ile Glu Lys Thr Ile Ser Lys Ala Lys Gly Gln
                 85                  90                  95

Pro Arg Glu Pro Gln Val Tyr Thr Leu Pro Pro Thr
            100                 105
```

<210> SEQ ID NO 10
<211> LENGTH: 189
<212> TYPE: PRT
<213> ORGANISM: Artificial Sequence
<220> FEATURE:
<223> OTHER INFORMATION: Fragment of the FC variant of an IgG anitbody

<400> SEQUENCE: 10

```
Ala Asp Lys Arg Val Glu Pro Lys Ser Cys Asp Lys Thr His Thr Cys
 1               5                  10                  15

Pro Pro Cys Pro Ala Pro Glu Leu Leu Gly Gly Pro Ser Val Phe Leu
             20                  25                  30

Leu Pro Pro Lys Pro Lys Asp Thr Leu Met Ile Ser Arg Thr Pro Glu
         35                  40                  45

Val Thr Cys Val Val Val Asp Val Ser His Glu Asp Pro Glu Val Lys
 50                  55                  60

Phe Asn Trp Tyr Val Asp Gly Val Glu Val His Asn Ala Lys Thr Lys
 65                  70                  75                  80

Pro Arg Glu Glu Gln Tyr Asn Ser Thr Tyr Arg Val Val Ser Val Leu
                 85                  90                  95

Thr Val Leu His Gln Asp Trp Leu Asn Gly Lys Glu Tyr Lys Cys Lys
            100                 105                 110

Val Ser Asn Glu Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Val
            180                 185
```

<210> SEQ ID NO 11
<211> LENGTH: 190
<212> TYPE: PRT
<213> ORGANISM: Artificial Sequence
<220> FEATURE:
<223> OTHER INFORMATION: Fragment of the FC variant of an IgG anitbody

<400> SEQUENCE: 11

```
Asn Val Asp Lys Arg Val Glu Pro Lys Ser Cys Asp Lys Thr His Thr
 1               5                  10                  15

Cys Pro Pro Cys Pro Ala Pro Glu Leu Leu Gly Gly Pro Ser Val Phe
             20                  25                  30
```

```
Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
 50                  55                  60

Lys Phe Asn Trp Tyr Val Asp Gly Val Glu Val His Asn Ala Lys Thr
 65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
                100                 105                 110

Lys Val Ser Asn Glu Ala Leu Pro Ala Pro Ile Glu Lys Thr Ile Ser
                115                 120                 125

Lys Ala Lys Gly Gln Pro Arg Glu Pro Gln Val Tyr Thr Leu Pro Pro
            130                 135                 140

Ser Arg Asp Glu Leu Thr Lys Asn Gln Val Ser Leu Thr Cys Leu Ile
145                 150                 155                 160

Lys Gly Phe Tyr Pro Ser Asp Ile Thr Val Glu Trp Glu Ser Asn Gly
                165                 170                 175

Gln Pro Glu Asn Asn Tyr Lys Thr Thr Pro Pro Val Leu Asp
                180                 185                 190
```

<210> SEQ ID NO 12
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 12

```
Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Ile Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205
```

```
Glu Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Ala Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Ala Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Leu Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Glu Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Val Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 14
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Leu Lys Asp Thr Leu Leu Ile Ser Arg Thr Pro Glu Val Thr Cys
    130                 135                 140

Val Val Val Asp Leu Ser His Glu Asp Pro Glu Val Lys Phe Asn Trp
145                 150                 155                 160

Phe Val Asp Gly Glu Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Thr Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Asn Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val Arg Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Glu Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Ile Lys Gly Phe Tyr
                245                 250                 255

Pro Ser Asp Ile Thr Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Glu Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 17
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Ser Ala Val Leu Gln Ser Ser Gly Leu Tyr Ser
    50                  55                  60

Leu Ser Ser Val Val Thr Val Pro Ser Cys Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Val Met Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 330
<212> TYPE: PRT
<213> ORGANISM: Artificial Sequence
<220> FEATURE:
<223> OTHER INFORMATION: FC variant of an IgG antibody
```

-continued

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Glu Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Phe His Pro
        115                 120                 125

Lys Pro Lys Asp Thr Leu Met Ile Ser Arg Thr Pro Glu Val Thr Cys
130                 135                 140

Val Val Val Asp Val Ser Tyr Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

-continued

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Glu Pro Ser Asn Thr Lys Ala Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Val Pro Ser Val Phe Leu Leu Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Ile Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Ser Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                325                 330
```

<210> SEQ ID NO 20
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 20

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Ile Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Thr Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 21

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Pro Thr Ser
             35                  40                  45

Gly Val His Thr Phe Pro Ala Val Leu Gln Ser Ser Gly Leu Tyr Ser
         50                  55                  60

Leu Gly Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

-continued

Arg Val Glu Pro Lys Ser Cys Asp Glu Thr His Thr Cys Pro Pro Cys
                100                 105                 110

Pro Ala Pro Glu Leu Leu Ala Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asp Trp
145                 150                 155                 160

Tyr Val Asp Gly Val Glu Val His Asn Ala Lys Thr Lys Pro Arg Glu
                165                 170                 175

Glu Gln Tyr Asn Gly Thr Tyr Arg Val Val Ser Val Leu Thr Val Leu
            180                 185                 190

His Gln Gly Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Phe Pro Pro
        115                 120                 125

-continued

Glu Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Tyr Tyr
                245                 250                 255

Pro Ser Asp Ile Ala Val Glu Trp Glu Ser Asn Gly Gln Pro Glu Asn
            260                 265                 270

Asn Tyr Lys Thr Ala Pro Pro Val Leu Asp Ser Asp Gly Ser Phe Phe
        275                 280                 285

Leu Tyr Ser Lys Leu Thr Val Asp Lys Ser Arg Trp Gln Leu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Pro Thr Ser
            35                  40                  45

Gly Val His Thr Phe Pro Ala Val Leu Gln Ser Ser Gly Leu Tyr Ser
        50                  55                  60

Leu Gly Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Glu Thr His Thr Cys Pro Pro Cys
            100                 105                 110

Pro Ala Pro Glu Leu Leu Ala Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asp Trp
145                 150                 155                 160

```
Tyr Val Asp Gly Val Glu Val His Asn Ala Lys Thr Lys Pro Arg Glu
            165                 170                 175

Glu Gln Tyr Asn Gly Ala Tyr Arg Val Val Ser Val Leu Thr Val Leu
        180                 185                 190

His Gln Gly Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Ala Gly Pro Ser Val Phe Leu Ile Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Gly Ala Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Thr Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 25
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Ile Pro Pro
    115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 26
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Thr Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 27
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 28
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Glu Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 29
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 30
<211> LENGTH: 330
<212> TYPE: PRT

<213> ORGANISM: Artificial Sequence
<220> FEATURE:
<223> OTHER INFORMATION: FC variant of an IgG antibody

<400> SEQUENCE: 30

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Leu Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 31
<211> LENGTH: 330
<212> TYPE: PRT
<213> ORGANISM: Artificial Sequence
<220> FEATURE:
<223> OTHER INFORMATION: FC variant of an IgG antibody
<400> SEQUENCE: 31 b;normal -continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 32
<211> LENGTH: 330
<212> TYPE: PRT
<213> ORGANISM: Artificial Sequence
<220> FEATURE:
<223> OTHER INFORMATION: FC variant of an IgG antibody

<400> SEQUENCE: 32
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65              70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
             130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Gly Ala Tyr Arg Val Val Ser Val Leu Thr Val Leu
             180                 185                 190

His Gln Asp Trp Leu Asn Gly Lys Glu Tyr Lys Cys Lys Val Ser Asn
             195                 200                 205

Lys Ala Leu Pro Ala Pro Ile Glu Lys Thr Ile Ser Lys Ala Lys Gly
             210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
                 260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
         290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                 325                 330
```

FC MUTANTS

CROSS-REFERENCE TO RELATED APPLICATION

This application claims the benefit of priority to U.S. Provisional Patent Application No. 61/259,457 filed on Nov. 9, 2009, the disclosure of which is incorporated herein by reference.

STATEMENT REGARDING FEDERALLY FUNDED RESEARCH

The Research Leading to the present invention was supported in part, by National Institutes of Health Grant No. CA 80757. Accordingly, the U.S. Government has certain rights in this invention.

FIELD OF THE INVENTION

The present invention relates to a novel method for designing therapeutic antibodies and vaccines for treatment of microbial infection, cancer and autoimmune disease.

BACKGROUND OF THE INVENTION

The mammalian immune system has evolved to defend the organism against pathogenic microbes, layering the specificity of adaptive responses on the ancestral pathways of innate immunity. This complexity exists to provide discrimination between self and non-self and to insure that immune responses are tightly regulated, thus avoiding autotoxicity and uncontrolled inflammation. Multiple checkpoints have been identified that function to insure an orderly progression through an immune response and thereby prevent the generation of self destructive processes. A common theme that has emerged from the study of these checkpoints is the requirement for the establishment of discrete thresholds that define narrow windows of response. One mechanism to achieve these thresholds is for the co-expression of receptors with common ligand binding properties but divergent signaling capacities, coupling activating receptors with an inhibitory counterpart thereby setting thresholds for immune cell activation (Ravetch, Fc receptors. In Fundamental Immunology, W. E. Paul, ed. (Philadelphia, Lippincott-Raven), pp. 685-700 (2003)).

Although cellular receptors for immunoglobulins were first identified nearly 40 years ago, their central role in the immune response was only discovered in the last decade. They are key players in both the afferent and efferent phase of an immune response, setting thresholds for B cell activation and antibody production, regulating the maturation of dendritic cells and coupling the exquisite specificity of the antibody response to effector pathways, such as phagocytosis, antibody dependent cellular cytotoxicity and the recruitment and activation of inflammatory cells. Their central role in linking the humoral immune system to innate effector cells has made them attractive immunotherapeutic targets for either enhancing or restricting the activity of antibodies in vivo.

The interaction of antibodies and antibody-antigen complexes with cells of the immune system effects a variety of responses, including antibody dependent cell-mediated cytotoxicity (ADCC) and complement dependent cytotoxicity (CDC), phagocytosis, inflammatory mediator release, clearance of antigen, and antibody half-life (reviewed in Daron, Annu Rev Immunol, 15, 203-234 (1997); Ward and Ghetie, Therapeutic Immunol, 2, 77-94 (1995); Ravetch and Kinet, Annu Rev Immunol, 9, 457-492 (1991)), each of which is incorporated herein by reference).

Antibody constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins (isotypes): IgA, IgD, IgE, IgG, and IgM, and several of these may be further divided into subclasses, e.g., IgG1, IgG2, IgG3, and IgG4; IgA1 and IgA2. The heavy chain constant regions that correspond to the different classes of immunoglobulins are called $\alpha$, $\delta$, $\in$, $\gamma$, and $\mu$, respectively. Of the various human immunoglobulin classes, human IgG1 and IgG3 mediate ADCC more effectively than IgG2 and IgG4.

Papain digestion of antibodies produces two identical antigen binding fragments, called Fab fragments, each with a single antigen binding site, and a residual "Fc" fragment, whose name reflects its ability to crystallize readily. The Fc region is central to the effector functions of antibodies. The crystal structure of the human IgG Fc region has been determined (Deisenhofer, Biochemistry, 20, 2361-2370 (1981), which is incorporated herein by reference). In human IgG molecules, the Fc region is generated by papain cleavage N-terminal to Cys, 226.

Several antibody functions are mediated by Fc receptors (FcRs), which bind the Fc region of an antibody. FcRs are defined by their specificity for immunoglobulin isotypes: Fc receptors for IgG antibodies are referred to as Fc$\gamma$R, for IgE as Fc$\in$FR, for IgA as Fc$\alpha$R and so on. Surface receptors for immunoglobulin G are present in two distinct classes—those that activate cells upon their crosslinking ("activation FcRs") and those that inhibit activation upon co-engagement ("inhibitory FcRs").

In all mammalian species studied to date, four different classes of Fc-receptors have been defined: Fc$\gamma$RI (CD64), Fc$\gamma$RII (CD32), Fc$\gamma$RIII (CDI6) and Fc$\gamma$RIV. Whereas Fc$\gamma$RI displays high affinity for the antibody constant region and restricted isotype specificity, Fc$\gamma$RII and Fc$\gamma$RIII have low affinity for the Fc region of IgG but a broader isotype binding pattern (Ravetch and Kinet, 1991; Hulett and Hogarth, Adv Immunol 57, 1-127 (1994)). Fc$\gamma$RIV is a recently identified receptor, conserved in all mammalian species with intermediate affinity and restricted subclass specificity (Mechetina et al., Immunogenetics 54, 463-468 (2002); Davis et al., Immunol Rev 190, 123-136 (2002); Nimmerjahn et al., (2005)).

Functionally there are two different classes of Fc-receptors: the activation and the inhibitory receptors, which transmit their signals via immunoreceptor tyrosine based activation (ITAM) or inhibitory motifs (ITIM), respectively (Ravetch, in Fundamental Immunology W. E. Paul, Ed. (Lippincott-Raven, Philadelphia, (2003); Ravetch and Lanier, Science 290, 84-89 (2000). The paired expression of activating and inhibitory molecules on the same cell is the key for the generation of a balanced immune response. Additionally, it has only recently been appreciated that the IgG Fc-receptors show significant differences in their affinity for individual antibody isotypes rendering certain isotypes more strictly regulated than others (Nimmerjahn et al., 2005).

The mouse expresses three activation Fc$\gamma$Rs, FcRI, FcRIII and FcRIV, oligomeric surface receptors with a ligand binding $\alpha$ subunit and an ITAM containing $\gamma$ subunit. The inhibitory receptor is Fc$\gamma$RIIB, a single chain receptor with an ITIM sequence found in the cytoplasmic tail of the ligand binding $\alpha$ chain. FcRIIB and FcRIII bind monomeric IgG with an affinity constant of $1\times10^6$; hence, under physiological conditions they do not bind monomeric IgG, but interact with multimeric IgG immune complexes with low affinity and high avidity. FcRIII and FcRIV are physiologically important activation FcRs for mediating inflammatory disease triggered by cytotoxic antibodies or pathogenic immune complexes. FcRIII is expressed on dendritic cells, NK cells, macrophages, monocytes, mast cells and neutrophils in the mouse, while FcRIV is found on dendritic cells, macrophages, monocytes and neutrophils. They are not found on B cells, T cells, red blood cells or platelets. FcRIIB is found on most hematopoeitic cells, including dendritic cells, B cells, macrophages, monocytes mast cells and neutrophils. It is not found on T cells or NK cells. FcRII and III have greater than 90% sequence identity in their extracellular, ligand binding domain, while FcRIV is most homologous to human FcRIIIA The situation in the human is analogous. There are three low-affinity activation FcRs for IgG-FcγRIIA, FcγRIIC and FcγRIIIA FcγRIIA and FcγRIIC are a single-chain low affinity receptors for IgG, with an ITAM sequence located in their cytoplasmic tail. They are expressed on dendritic cells, macrophages, mast cells, monocytes and neutrophils. They are 90% homologous in their extracellular domains to the human inhibitory FcRIIB molecule, which has an ITIM sequence in its cytoplasmic domain, expressed on dendritic cells, B cells, macrophages, mast cells, neutrophils, monocytes but not NK cells or T cells. FcRIIIA is an oligomeric activation receptor consisting of a ligand binding subunit and an ITAM containing γ or ξ subunit. It is expressed on NK cells, macrophages and mast cells. It is not expressed on neutrophils, B cells or T cells. In addition, a receptor with greater than 95% sequence identity in its extracellular domain called FcRIIIB is found on human neutrophils as a GPI-anchored protein. It is capable of binding immune complexes but not activating cells in the absence of association with an ITAM containing receptor like FcRIIA. FcRII and FcRIII are about 70% identical in their ligand binding extracellular domains.

Thus, in the human, IgG antibodies interact with four distinct low-affinity receptors—three of which are capable of activating cellular responses, FcRIIA, FcRIIC and FcRIIIA, one of which is inhibitory, FcRIIB and one of which will bind IgG complexes but not trigger cellular responses, FcRIIIB Macrophages expresses FcRIIA, FcRIIB and FcRIIIA, neutrophils express FcRIIA, FcRIIB and FcRIIIA, while NK cells express only FcRIIIA The biological activity of an IgG antibody will thus depend on the specific interactions with activation, inhibition and inert low-affinity FcRs, differentially expressed on distinct cell types.

Diversification of IgG subclasses is most strikingly observed in mammals where detailed characterization of four subclasses has been described (Litman et al., *Annu Rev Immunol* 17, 109-47 (1999)). In both rodents and primates these subclasses display differential abilities to mediate effector responses, such as antibody dependent cytotoxicity, phagocytosis and release of inflammatory mediators (Burton and Woof, *Adv Immunol* 51, 1-84 (1992); Ravetch, (2003) pp. 685-700; Ravetch and Bolland, *Annu Rev Immunol* 19, 275-90 (2001)). Skewing of the expression of IgG subclasses is regulated by both the antigen and cytokine milieu, such that IL-4 preferentially induces switching to IgG1 and IgE, while TGF-β induces switching to IgG2b and IgA (Finkelman et al., *Annu Rev Immunol* 8, 303-33. (1990); Stavnezer, *J Immunol* 155, 1647-51 (1995); Snapper and Mond, *Immunol Today* 14, 15-7 (1993)). Thymic dependent antigens primarily result in IgG1, 2a and 2b responses; in contrast, thymic independent antigens typically lead to IgG3 accumulation (Mond et al., *Curr Opin Immunol* 7, 349-54 (1995)). Further distinctions among the subclasses occurs in response to T cell derived responses with $T_{H1}$ cytokines resulting in IgG2a, 2b and 3 switching, while $T_{H2}$ cytokines lead to IgG1 and IgE dominated responses (Mosmann, and Coftman, *Annu Rev Immunol* 7, 145-73 (1989)). Among the IgG subclasses, IgG2a and 2b are generally considered to be the most potent at activating effector responses and have been found to dominate in both anti-viral and autoimmune conditions (Coutelier et al., *J Exp Med* 165, 64-9 (1987); Markine-Goriaynoff and Coutelier, *J Virol* 76, 432-5. (2002); Fossati-Jimack et al., *J Exp Med* 191, 1293-302 (2000); Uchida et al., (2004)).

Immune complexes consisting of IgG antibodies bind to activating Fc receptors (FcR) and inhibitory FcRs that are expressed by innate immune effector cells such as basophils, mast cells, neutrophils, moncytes and macrophages, in which they trigger the indicated effector responses. Binding of immune complexes to FcRs on dendritic cells results in phagocytosis and presentation of antigenic peptides on MHC class I and class II molecules. Antigen-specific $CD8^+$ cytotoxic T cells, $CD4^+$ helper T cells or regulatory T cells ($T_{Reg}$ cells) that recognize these peptide-MHC complexes become activated and mediate various effector functions such as killing of virus-infected cells, modulation of immune responses or providing T-cell help for antigen-specific B cells. B cells only express inhibitory low-affinity FcR for IgG (FcγIIB), which regulates activation signals transduced by the B-cell receptor (BCR). On plasma cells, which produce high levels of antigen-specific antibodies, BCR expression is very low or absent, resulting in exclusive triggering of inhibitory signaling pathways which can result in apoptosis on those cells.

The family of Fc receptors (FcRs) for IgG (FcγRs) provides a prime example of how simultaneous triggering of activating and inhibitory signaling pathways sets thresholds for cell activation and thus generates a well-balanced immune response. (Ravetch & Lanier, Science 290:84-89 (2000)). Indeed, in a variety of human autoimmune diseases, such as arthritis and systemic lupus erythematosus (SLE), aberrant expression or the presence of allelic variants of FcγRs with altered functionality have been observed that contribute to the pathogenesis of these diseases. In particular, expression of the inhibitory FcγRIIB receptor on B cells has been linked to susceptibility to autoimmune diseases such as lupus by altering B cell homeostasis and thereby contributing to the loss of tolerance to self antigens.

The inhibitory FcγRIIB is the most broadly expressed FcγR, and is present on virtually all leukocytes with the exception of NK cells and T cells. Because of the broad expression pattern, it is not surprising that genetic deletion of this negative regulator results in complex phenotypic changes affecting innate and adaptive immune responses.

Antibody binding to cellular FcγRs efficiently induces pro-inflammatory responses that lead to the removal of virus-infected or malignant cells, but it can also lead to the destruction of healthy tissues during autoimmune responses. Therefore, antibody specificity, as well as class switching to antibody isotypes that efficiently trigger pro-inflammatory reactions through their interaction with cellular FcγRs, have to be tightly controlled. Groundbreaking work over the last few years has established that several central and peripheral checkpoints exist throughout B-cell development to prevent the generation of autoreactive antibodies (Goodnow et al, *Nature* 435, 590-597 (2005)). On a molecular level, gene-deletion studies in mice have been instrumental in identifying several proteins (including the inhibitory FcγRIIB) that are involved in regulating B-cell activity.

One common theme that emerged from these studies is the importance of the ITIMs found in the cytoplasmic domains of these proteins (Amigorena et al, *Science* 256, 1808-1812

(1992); and Muta et al, *Nature* 369, 340 (1994)). Simultaneous triggering of ITIM-containing proteins with the BCR results in the recruitment of phosphatases such as SHIP (SH2—domain-containing inositol polyphosphate 5' phosphatase) and SHP1 (SH2-domain-containing protein tyrosine phosphatase 1) that interfere with activating signalling pathways by hydrolysing phosphoinositide intermediates (Bolland. & Ravetch, *Adv. Immunol.* 72, 149-177 (1999). Nitschke. & Tsubata, *Trends Immunol.* 25, 543-550 (2004), Ono et al, *Nature* 383, 263-266 (1996), Ono et al, *Cell* 90, 293-301 (1997)). This prevents the recruitment of pleckstrin homology (PH)-domain-containing kinases, such as BTK or PLCγ, to the cell membrane, thereby diminishing downstream events such as the increase in intracellular calcium levels. Thus, deletion of these regulatory proteins results in a lower threshold for B-cell activation and stronger activating signals after BCR crosslinking (Nitschke. & Tsubata, (2004)).

The importance of the inhibitory FcγRIIB in modulating B-cell activity and humoral tolerance is supported by studies of mice and humans. Decreased or absent expression of FcγRIIB resulted in the development or exacerbation of autoimmune diseases and several mechanisms responsible for this reduced expression were identified. Regardless of the model system studied, FcγRIIB has emerged as a late checkpoint during peripheral B-cell development that acts at the level of class switched B cells or antibody producing plasmablasts or plasma cells. Given the incomplete purging of autoreactive B cells from the immature repertoire in the bone marrow and the de novo generation of these cells during the process of affinity maturation, late peripheral checkpoints are of utmost importance.

Recent data suggests that the inhibitory FcγRIIB is important for regulating plasma-cell survival itself. The first evidence that the isolated triggering of FcγRIIB can induce apoptosis in B cells was reported 10 years ago. Co-engagement of the BCR and FcγRIIB in SHIP deficient B cells induced apoptosis (Ono et al, (1996), Ono et al, (1997)). Similarly, the homo-oligomerization of FcγRIIB resulted in increased levels of B-cell death, and it was shown later that a signaling pathway dependent on BTK, JNK1 and cABL, but independent of SHIP and ITIM, was responsible for this phenotype (Pearse et al, *Immunity* 10, 753-760 (1999) and Tzeng et al, *J. Biol. Chem.* 22, 22 (2005)). It was suggested that this scenario might arise during the germinal-centre reaction, in which B cells are in close contact with immune complexes presented on the surface of FDCs. Whereas B cells that generate a higher-affinity BCR will receive signals from both the BCR and FcγRIIB, B cells that lose affinity for the cognate antigen will only receive signals through FcγRIIB and will therefore be deleted.

Another situation in which a B cell expresses virtually no BCR and high levels of FcγRIIB is the terminally differentiated plasma cell. Plasma cells reside predominantly in niches in the bone marrow, where they have to receive survival signals from stromal cells (Radbruch et al, *Nature Rev. Immunol.* 6, 741-750 (2006)). If deprived of these anti-apoptotic signals, plasma cells rapidly die owing to pro-apoptotic signals triggered by a constant endoplasmic-reticulum-stress response induced by the continuous production of antibodies. One current conundrum is how the limited number of niches available in the bone marrow can accommodate the vast number of antigen-specific plasma cells that are necessary to protect the body from all types of pathogens (Radbruch et al, (2006)). How newly generated plasma cells gain access to these niches has remained a matter of debate, and models such as competitive dislocation have been proposed to explain this problem (plasma blasts and mobilization of resident plasma cells in a secondary immune response. (Odendahl et al, *Blood* 105, 1614-1621 (2005)). The pro-apoptotic signals triggered by isolated FcγRIIB crosslinking by immune complexes on plasma cells might be another elegant solution to this problem (Ravetch & Nussenzweig, *Nature Immunol.* 8, 337-339 (2007); and Xiang et al, *Nature Immunol.* 8, 419-429 (2007)). Immune complexes generated de novo during an immune response could bind to plasma cells in the bone marrow and induce apoptosis on a fraction of cells, thus making space for newly generated plasma cells. Indeed, secondary immunizations with a new antigen result in reduced numbers of bone marrow plasma cells that are specific for the primary antigen (Xiang et al, (2007)).

Interestingly, plasma cells from autoimmune-prone mouse strains show absent or strongly reduced expression of FcγRIIB, and are resistant to induction of apoptosis. By contrast, restoration or overexpression of the inhibitory receptor could correct this defect (Xiang et al, (2007)). Therefore, the failure to control plasma-cell persistence resulting from impaired FcγRIIB expression levels might account for their large number in autoimmune-prone mouse strains and ultimately for the development of chronic autoimmune disease. Correction of FcγRIIB expression levels might be a promising approach to interfere with autoimmune processes and to restore tolerance.

Therefore, in autoimmune conditions, such as lupus or rheumatoid arthritis, hyperactivation of B cells is observed with inappropriate production of autoantibodies. These B cells have escaped from the normal regulation imposed by the inhibitory FcRIIB receptor. Co-engagement of activation cell surface B cell molecules with FcRIIB would address this problem and provide a means to reduce B cell activation. Methods and means to accomplish this are presented below.

DCs are the most potent antigen-presenting cells and can efficiently prime cellular immune responses. Besides this well-established function it is has become clear that during the steady state, these cells are actively involved in the maintenance of peripheral T-cell tolerance (Ono et al, *Nature* 383, 263-266 (1996)). Thus, targeting antigens to DCs in vivo without the addition of co-stimulatory signals, such as those that trigger CD40 or Toll-like receptors, leads to the deletion or functional inactivation of antigen-specific CD4+ and CD8+ T cells (Dudziak et al, *Science* 315, 107-111 (2007); Hawiger et al, *J. Exp. Med.* 194, 769-779 (2001); Hawiger et al, *Immunity* 20, 695-705 (2004); Kretschmer et al, *Nature Immunol.* 6, 1219-1227 (2005); and Steinman et al, *Ann. NY Acad. Sci.* 987, 15-25 (2003)). This suggests that potentially self-reactive T cells that escaped deletion by central tolerance mechanisms in the thymus, will be rendered inactive upon recognition of self antigens on DCs in the periphery. In addition, there is evidence that antigen presentation to CD4+ T cells by DCs under tolerogenic conditions can induce regulatory T cells de novo (Kretschmer et al, (2005)). Therefore, the maturation state of DCs has to be tightly controlled to prevent both the initiation of self-destructive responses and the generation of regulatory T cells during a protective antimicrobial immune response. A great number of activating and inhibitory cellsurface proteins involved in the regulation of DC activation have been identified (Schuurhuis et al, *Int. Arch. Allergy Immunol.* 140, 53-72 (2006)). Among them, the family of activating and inhibitory FcγRs has been shown to be of central importance for setting a threshold for DC activation and in the modulation of the adaptive cellular immune responses. This, however, is not the only function of FcγRs on DCs, as they are also important for endocytosis and/or phagocytosis of immune complexes and presentation of antigen-derived peptides on MHC molecules (Woelbing et al, *J. Exp. Med.* 203, 177-188 (2006)). Therefore, FcγRs control three functions that are of central importance to any immune response initiated by DCs: antigen uptake, antigen presentation and cell activation.

Most FcγRs can only interact with antibodies in the form of immune complexes resulting in high-avidity binding. During an active immune response, a large number of immune complexes are generated owing to the priming of antigen-specific B cells. Several studies have shown that immune complexes are potent activators of DCs and are able to prime stronger immune responses than antigen alone (Regnault et al, *J. Exp. Med.* 189, 371-380 (1999); Dhodapkar et al, *J. Exp. Med.* 195, 125-133 (2002); 88. Groh et al, *Proc. Natl. Acad. Sci. USA* 102, 6461-6466 (2005); 89. Rafiq et al, *J. Clin. Invest.* 110, 71-79 (2002); and 90. Schuurhuis et al, *J. Immunol.* 176, 4573-4580 (2006). Importantly, FcγR-dependent immune-complex internalization not only resulted in MHC-class-II-restricted antigen presentation but also in cross-presentation on MHC class 1 molecules, thereby priming both CD4 and CD8 T-cell responses (Regnault et al, (1999)). The magnitude of this response is controlled by the inhibitory FcγRIIB, as DCs derived from Fcgriib-knockout mice generate stronger and longer-lasting immune responses in vitro and in vivo (Bergtold et al, *Immunity* 23, 503-514 (2005); and Kalergis & Ravetch J. Exp. Med. 195, 1653-1659 (2002)). More importantly, FcγRllBdeficient DCs or DCs incubated with a monoclonal antibody that blocks immune complex binding to FcγRIIB showed a spontaneous maturation (Boruchov et al, *J. Clin. Invest.* 115, 2914-2923 (2005); and Dhodapkar et al, *Proc. Natl. Acad. Sci. USA* 102, 2910-2915 (2005)). This implies that the inhibitory FcγR not only regulates the magnitude of cell activation but also actively prevents spontaneous DC maturation under non-inflammatory steady-state conditions. Indeed, low levels of immune complexes can be identified in the serum of healthy individuals, emphasizing the importance of regulatory mechanisms that prevent unwanted DC activation (Dhodapkar et al, (2005)).

In situations in which a maximal immune response is desirable, such as immunotherapy of malignancies or microbial infections, blocking FcγRIIB activity might be a novel way to obtain greater therapeutic efficacy. Along these lines, it has been demonstrated that the genetic deletion of the gene encoding FcγRIIB results in the priming of more antigen-specific T cells (Kalergis & Ravetch (2002)). Moreover, current approaches for targeting antigens to DCs in vivo by genetic fusion of the antigen to an antibody Fc fragment rely on an antibody mutant that does not bind to FcγRs to prevent FcγR-mediated modulation of cell activity. With the availability of antibody variants with enhanced binding to either activating or inhibitory FcγRs, however, it might become possible to integrate an additional activating or inhibitory second signal into the antibody-antigen fusion protein (Lazar et al, *Proc. Natl. Acad. Sci. USA* 103, 4005-4010 (2006); and Shields et al, *J. Biol. Chem.* 276, 6591-6604 (2001)). Depending on the application, this would permit the generation of either tolerogenic or immunogenic responses without adding secondary reagents. As will be discussed later, mouse models in which the mouse FcγRs have been replaced with their human counterparts (referred to as FcγR humanized mice) will be essential to test these optimized antibody variants in vivo.

In addition to its expression on B cells, the inhibitory FcγRIIB is expressed on innate immune effector cells, such as mast cells, granulocytes and macrophages. As these cells have the capacity to trigger strong pro-inflammatory responses, their activation needs to be tightly controlled. In the case of antibody-mediated responses, such as phagocytosis, ADCC, allergic reactions and release of pro-inflammatory mediatiors, this is the function of the inhibitory FcγRIIB This crucial role is exemplified by enhanced macrophage responses in Fcgriib-knockout mice in models of collagen-induced arthritis and immune-complex-mediated alveolitis. (Clynes et al., *J. Exp. Med.* 189:179-185 (1999); Yuasa et al, *J. Exp. Med.* 189:187-194 (1999)).

Recent studies have demonstrated that the inhibitory receptor contributes a varying level of negative regulation depending on the specific IgG subclass that is bound to the receptor. (Nimmerjahn & Ravetch, *Science* 310, 1510-1512 (2005)). This is consistent with the observation that different IgG subclasses have different activities in vivo. For example, in a variety of mouse model systems, IgG2a or IgGb antibody subclasses are more active than IgG1 or IgG3. (Nimmerjahn et al., *Immunity* 23, 41-51 (2005)). Whereas IgG1 shows the strongest level of FcγRIIB-mediated negative regulation, the activity of IgG2a and IgG2b was increased less dramatically by the absence of this receptor. (Nimmerjahn & Ravetch, (2005)). This can be explained by the differences in the affinity of these isotypes for the different activating and inhibitory FcγRs. This ratio of affinities of a given IgG subclass for the activating versus the inhibitory receptor has been termed the A/I-ratio and it has emerged as a good predictive value for the activity of a specific IgG subclass in vivo (Nimmerjahn et al., *Immunity* 23, 41-51 (2005); Nimmerjahn & Ravetch, (2005)). These studies indicate that the effector cells responsible for mediating the activity of the different IgG subclasses express both activating and the inhibitory FcγRs. As NK cells lack FcγRIIB expression this argues against a role for NK cells as the responsible effector cell in mice in vivo. Indeed, myeloid cells that abundantly express FcγRIIB have been suggested to be the responsible effector-cell type in models of ADCC and SLE (Uchida et al., *J Exp Med* 199, 1659-69 (2004); Begtold, *J. Immunol.* 177, 7287-7295 (2006)).

Accordingly, there is an immediate need for improved reagents, methods and systems for designing therapeutic antibodies and vaccines for treatment of autoimmune disease.

SUMMARY OF THE INVENTION

The present invention fills the foregoing need by providing an advantageous strategy for inhibiting the activation of autoreactive lymphocytes as well as effector cells by providing for antibody Fc variants with preferential binding to the inhibitory FcRIIB molecule.

The present invention represents an important improvement over prior art efforts to regulate antibody mediated immune responses. The present invention, by recognizing the inhibitory role of FcγRIIB in myeloid and lymphoid cell activation and B cell survival provides for Fc mutant inhibitory antibodies which permit binding of the inhibitory antibody or variant thereof with its FcγRIIB receptor, thereby reversing the activation state of myeloid and lymphoid cells or inducing B cell apoptosis.

The present invention, by recognizing that the inhibitory activity of an antibody or variant thereof can be predicted, provides a method in which one of skill in the art can by: (a) determining a binding affinity of the antibody to Fc activating receptors, (b) determining a binding affinity of the antibody to a Fc inhibitory receptor, and (c) calculating the ratio (A/I ratio) of said activating binding affinity to said inhibitory binding affinity, predict the in vivo activity of an antibody or variant wherein the magnitude of said ratio is an indication of the inhibitory activity of the antibody and predictive of its in vivo. One aspect of the present invention provides a general and widely applicable method of selecting a inhibitory antibody or variant thereof out of a plurality of antibodies comprising: comparing the A/I ratios of the plurality of antibodies; and selecting the inhibitory antibody or variant thereof with the an A/I ratio less than one (1), to permit binding of the inhibitory antibody or variant thereof with its FcγRIIB receptor, combining this variant Fc region with an antigen recognition domain, such as an Fab, to a defined activation receptor on the target cell and thus reducing the activation state of that cell.

In this aspect of the present invention provides a method of selecting one or more antibodies or variants thereof with reduced cytotoxic activity or perhaps "non-cytotoxic" activity comprising determining the A/I ratio of a plurality of antibodies or variants thereof and selecting those antibodies or variants thereof with a A/I ratio of less than 1.

In some embodiments, the inhibitory antibody is a human inhibitory antibody. In this embodiment of the invention the Fc activating receptor is selected from the group consisting of FcγRII and FcγRIII, and an Fc inhibitory receptor is FcγRIIB A preferred embodiment of the present invention provides that the human FcγRII activating receptor is FcγRIIA or FcγRIIC, wherein the human FcγRIII activating receptor is FcγRIIIA, and wherein the human FcγRII inhibitory receptor is FcγRIIB.

Another embodiment of the present invention provides that the inhibitory antibody is a chimeric antibody. Another embodiment of the present invention provides that the inhibitory antibody is a humanized antibody.

In some embodiments, the A/I ratio is determined by one or more quantitative assays, including competition or sandwich ELISA, a radioimmunoassay, a dot blot assay, a fluorescence polarization assay, a scintillation proximity assay, a homogeneous time resolved fluorescence assay, a resonant mirror biosensor analysis, and a surface plasmon resonance analysis. In the competition or sandwich ELISA, the radioimmunoassay, or the dot blot assay the A/I ratio can be determined by coupling the assay with a statistical analysis method, such as, for example, Scatchard analysis. Scatchard analysis is widely known and accepted in the art and is described in, for example, Munson et al., *Anal Biochem,* 107:220 (1980).

Another aspect of the present invention provides a purified modified antibody comprising an IgG Fc region, the modified antibody having a lower A/I ratio as compared to the unmodified antibody.

In some embodiments, the purified modified antibody comprises a human IgG1, IgG2, IgG3 or IgG4 Fc region, wherein the modified antibody binds to a human Fc activating receptor selected from the group consisting of FcγRII and FcγRIII, and wherein the modified antibody binds to a human FcγRII inhibitory receptor. One embodiment of the invention provides that the modified antibody has an increased inhibitory activity in vitro. A preferred embodiment of the present invention provides that the human FcγRII activating receptor is FcγRIIA (including 131H and 131R variants) or FcγRIIC, wherein the human FcγRIII activating receptor is FcγRIIIA (including FcγRIIIA FF and FcγRIIIA FV variants), and wherein the human FcγRII inhibitory receptor is FcγRIIB.

In another embodiment of the present invention, the purified modified antibody is either derived from a naturally occurring antibody or is expressed in a cell line.

In another embodiment of the present invention, the purified modified antibody comprising an IgG Fc region, the modified antibody having a lower A/I ratio as compared to the unmodified antibody, wherein said modified antibody has both greater binding to an inhibitory Fc receptor and about the same or reduced binding to an activating receptor as compared to the unmodified antibody.

In another embodiment of the present invention, the purified modified antibody is an amino acid sequence comprising a fragment consisting of amino acids 215-396 of SEQ ID NO: 1, wherein in said fragment, amino acids corresponding to amino acids at positions 215, 326, 359, and 396 of SEQ ID NO: 1 are different from said amino acids present in SEQ ID NO: 1.

In another embodiment of the present invention, the purified modified antibody is an amino acid sequence comprising a fragment consisting of amino acids 215-396 of SEQ ID NO: 1, wherein in said fragment (SEQ ID NO: 8), amino acids corresponding to amino acids at positions 215, 326, 359, and 396 of SEQ ID NO: 1 are different from said amino acids present in SEQ ID NO: 1, wherein further, the amino acid in said fragment corresponding to the amino acid at position 215 of SEQ ID NO: 1 is isoleucine, the amino acid in said fragment corresponding to the amino acid at position 326 of SEQ ID NO: 1 is glutamate, the amino acid in said fragment corresponding to the amino acid at position 359 of SEQ ID NO: 1 is alanine; and the amino acid in said fragment corresponding to the amino acid at position 396 of SEQ ID NO: 1 is leucine.

In another embodiment of the present invention, the purified modified antibody is an amino acid sequence comprising a fragment consisting of amino acids 247-354 of SEQ ID NO: 1, wherein in said fragment, amino acids corresponding to amino acids at positions 247, 252, 266, 278, 302, and 354 of SEQ ID NO: 1 are different from said amino acids present in SEQ ID NO: 1.

In another embodiment of the present invention, the purified modified antibody is an amino acid sequence comprising a fragment consisting of amino acids 247-354 of SEQ ID NO: 1, wherein in said fragment (SEQ ID NO: 9), amino acids corresponding to amino acids at positions 247, 252, 266, 278, 302, and 354 of SEQ ID NO: 1 are different from said amino acids present in SEQ ID NO: 1 wherein further, the amino acid in said fragment corresponding to the amino acid at position 247 of SEQ ID NO: 1 is leucine, the amino acid in said fragment corresponding to the amino acid at position 252 of SEQ ID NO: 1 is leucine, the amino acid in said fragment corresponding to the amino acid at position 266 of SEQ ID NO: 1 is leucine, the amino acid in said fragment corresponding to the amino acid at position 278 of SEQ ID NO: 1 is phenylalanine, the amino acid in said fragment corresponding to the amino acid at position 302 of SEQ ID NO: 1 is glutamate; and the amino acid in said fragment corresponding to the amino acid at position 354 of SEQ ID NO: 1 is threonine.

In another embodiment of the present invention, the purified modified antibody is an amino acid sequence comprising a fragment consisting of amino acids 211-399 of SEQ ID NO: 1, wherein in said fragment, amino acids corresponding to amino acids at positions 211, 243, 326, and 399 of SEQ ID NO: 1 are different from said amino acids present in SEQ ID NO: 1.

In another embodiment of the present invention, the purified modified antibody is an amino acid sequence comprising a fragment consisting of amino acids 211-399 of SEQ ID NO: 1, wherein in said fragment (SEQ ID NO: 10), amino acids corresponding to amino acids at positions 211, 243, 326, and 399 of SEQ ID NO: 1 are different from said amino acids present in SEQ ID NO: 1, wherein further, the amino acid in said fragment corresponding to the amino acid at position 211 of SEQ ID NO: 1 is alanine, the amino acid in said fragment corresponding to the amino acid at position 243 of SEQ ID NO: 1 is leucine, the amino acid in said fragment corresponding to the amino acid at position 326 of SEQ ID NO: 1 is glutamate; and the amino acid in said fragment corresponding to the amino acid at position 399 of SEQ ID NO: 1 is valine.

In another embodiment of the present invention, the purified modified antibody is an amino acid sequence comprising a fragment consisting of amino acids 210-399 of SEQ ID NO:1, wherein in said fragment (SEQ ID NO: 11), amino acids corresponding to amino acids at positions 210, 285, 326, 369, and 378 of SEQ ID NO: 1 are different in which lysine at position 210 is replaced by asparagine, histidine at position 285 is replaced by arginine, lysine at position 326 is replaced by glutamic acid, tyrosine at position 369 is replaced by isoleucine, and alanine at position 378 is replaced by threonine.

In another embodiment of the present invention, the purified modified antibody has a higher affinity to FcγRIIB than a SEQ ID NO: 1.

In another embodiment of the present invention, the purified modified antibody has a lower affinity to at least one of FcγRI, FcγRIIA$^{131H}$, FcγRIIA$^{131R}$, FcγIIIA FF, and FcγIIIA FV than SEQ ID NO: 1.

In another embodiment of the present invention, the purified modified antibody has a lower A/I ratio or lower FcγRIIA$^{131H}$/FcγRIIB A/I ratio or lower FcγRIIA$^{131R}$/FcγRIIB A/I ratio than SEQ ID NO: 1.

In another embodiment of the present invention, the purified modified antibody is a monoclonal antibody.

In another embodiment of the present invention, the purified modified antibody is a humanized antibody.

In another embodiment of the present invention, the purified modified antibody is a human antibody.

Another embodiment of the present invention provides for a method of inhibiting an immune response of a cell expressing an FcγRIIB receptor and at least one of FcγRI, FcγRIIA$^{131H}$, FcγRIIA$^{131R}$, FcγIIIA FF, and FcγIIIA FV receptors, the method comprising administering to the cell said purified modified antibody having a lower A/I ratio between said at least one of FcγRI, FcγRIIA$^{131H}$, FcγRIIA$^{131R}$, FcγIIIA FF, and FcγIIIA FV receptors and FcγRIIB receptor. In one embodiment of the present invention said cell is an effector cell. In one embodiment of the present invention said cell is a macrophage.

These and other aspects of the invention will be better understood by reference to the Drawings, Detailed Description, and Examples.

BRIEF DESCRIPTION OF THE DRAWINGS

FIG. 1 illustrates surface Plasmon resonace values for an unmodified human IgG1 Fc and four Fc variants.

DESCRIPTION OF THE INVENTION

Figure 2:
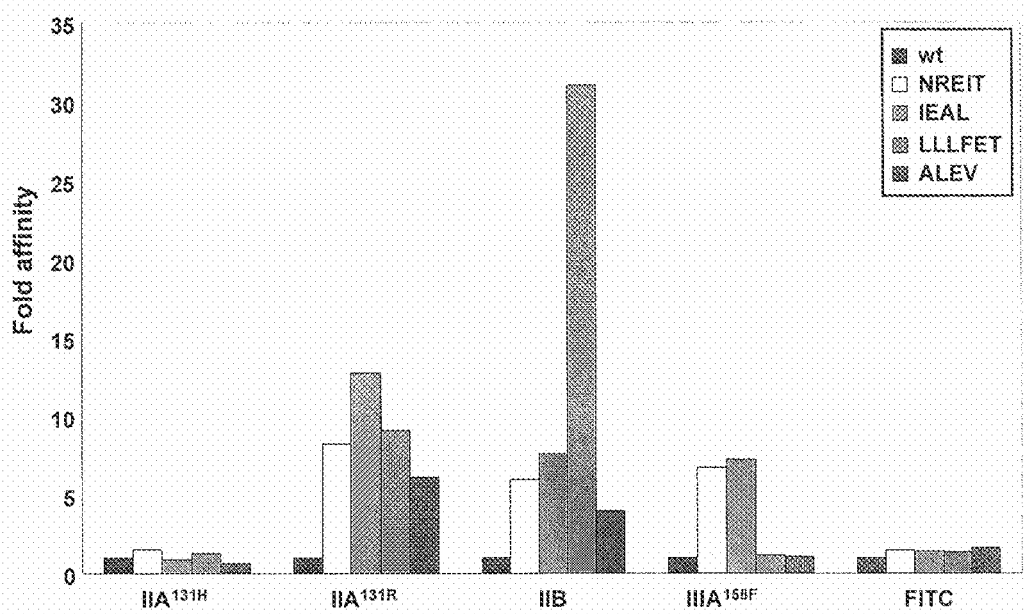
FIG. 2 illustrates the changes in binding affinity for four Fc variants to the human inhibitory Fc receptor, FcγRIIB.
Figure 3:
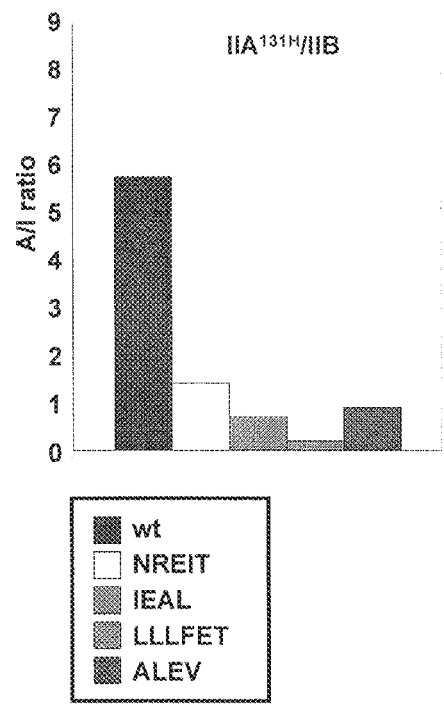
FIG. 3 illustrates the change in A/I ratio for four human Fc variants for the IIA and IIIA activation receptors compared to the inhibitory FcγRIIB receptor.
Figure 4:
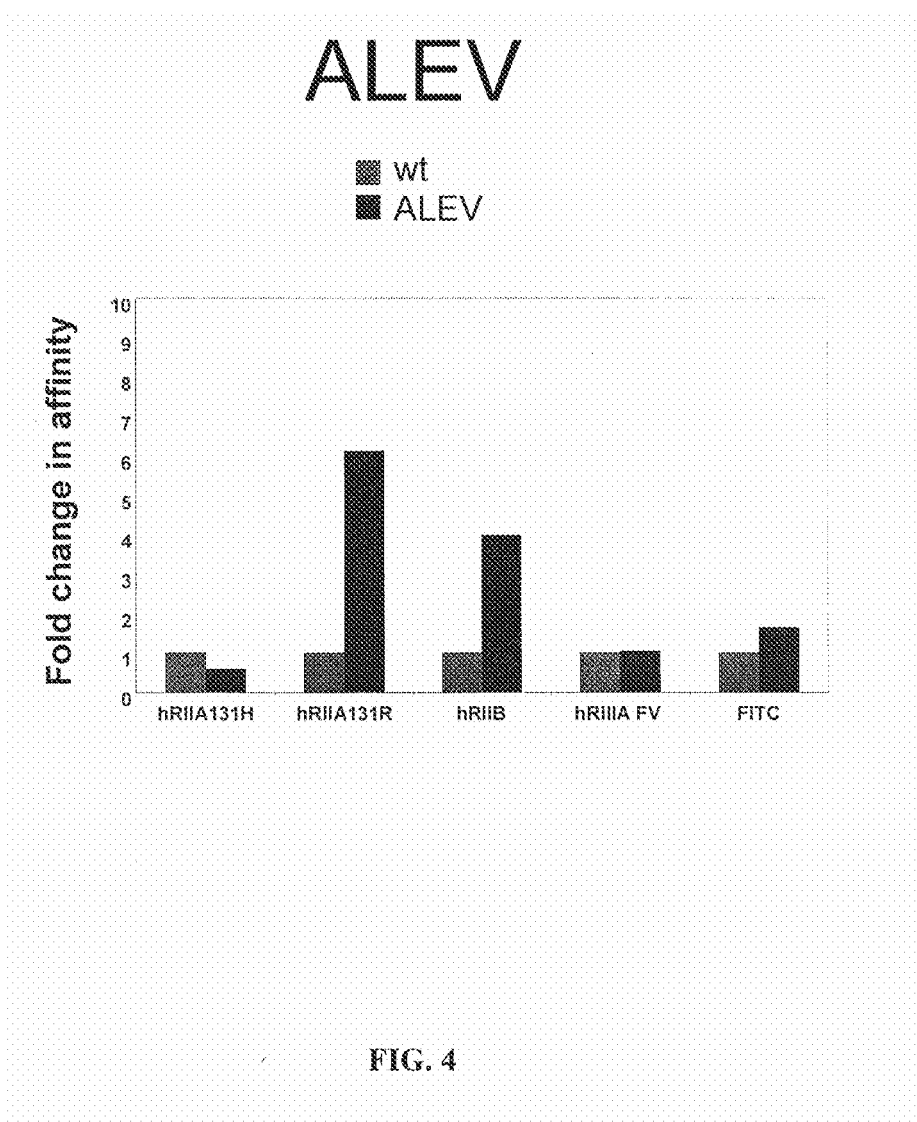
FIG. 4 illustrates the change in the affinity of the ALEV variant [SEQ ID NO: 13] to the inhibitory FcγRIIB receptor.
Figure 5:
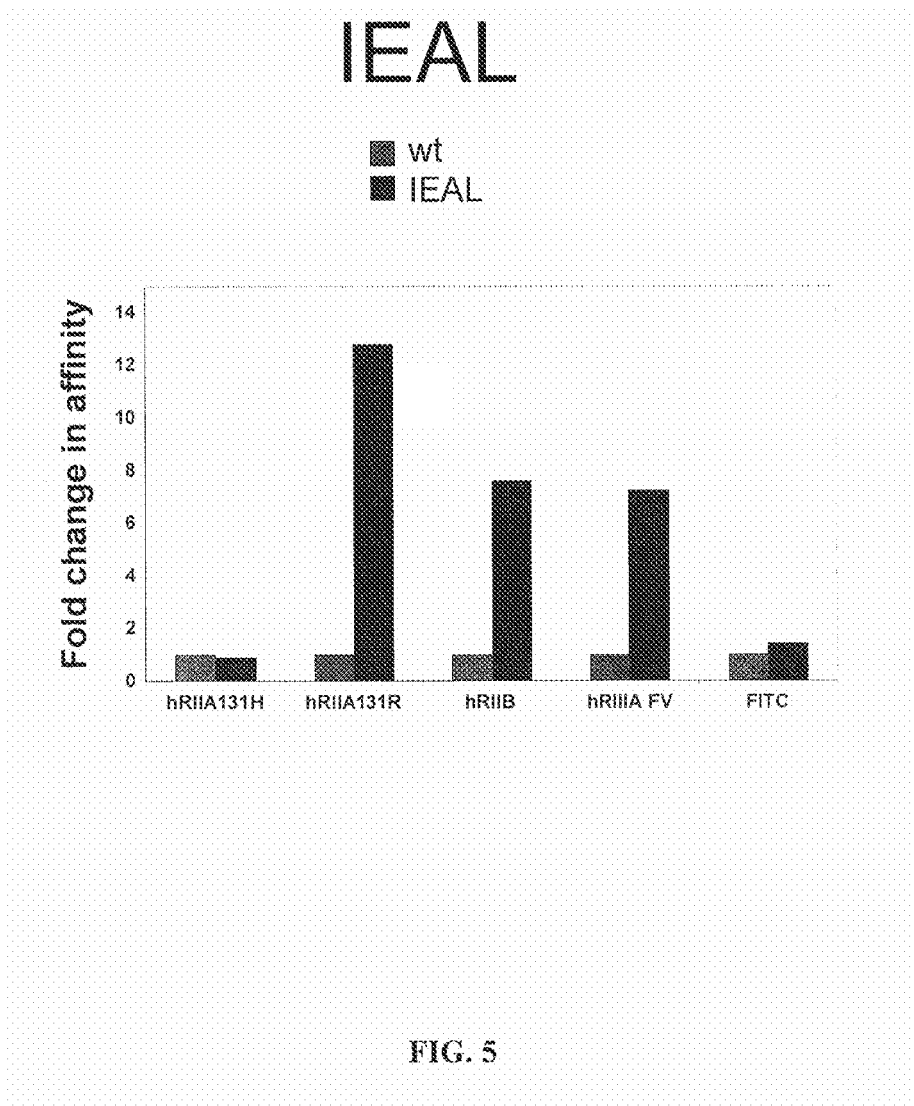
FIG. 5 illustrates the change in the affinity of the IEAL variant [SEQ ID NO: 12] to the human FcγRIIB receptor.
Figure 6:
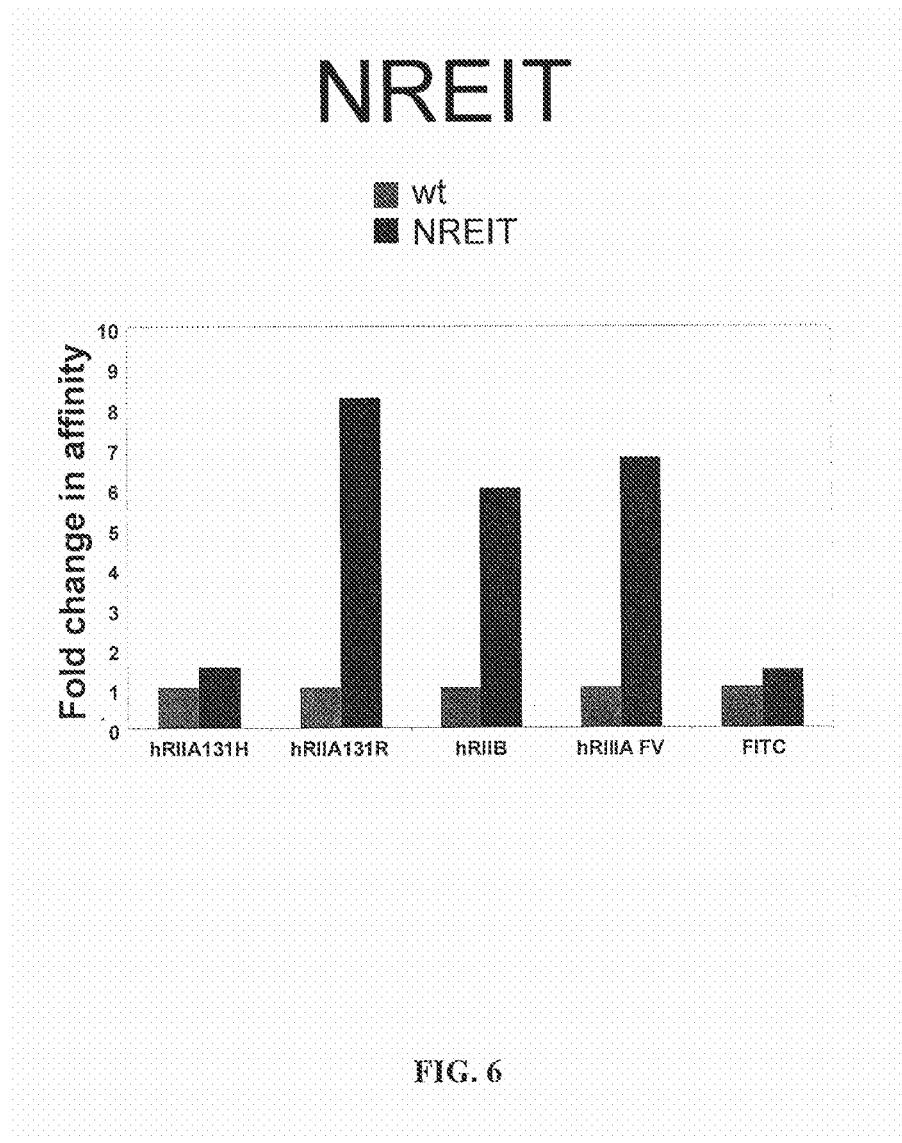
FIG. 6 illustrates the change in the affinity of the NREIT variant [SEQ ID NO: 15] to the FcγRIIB receptor.
Figure 7:
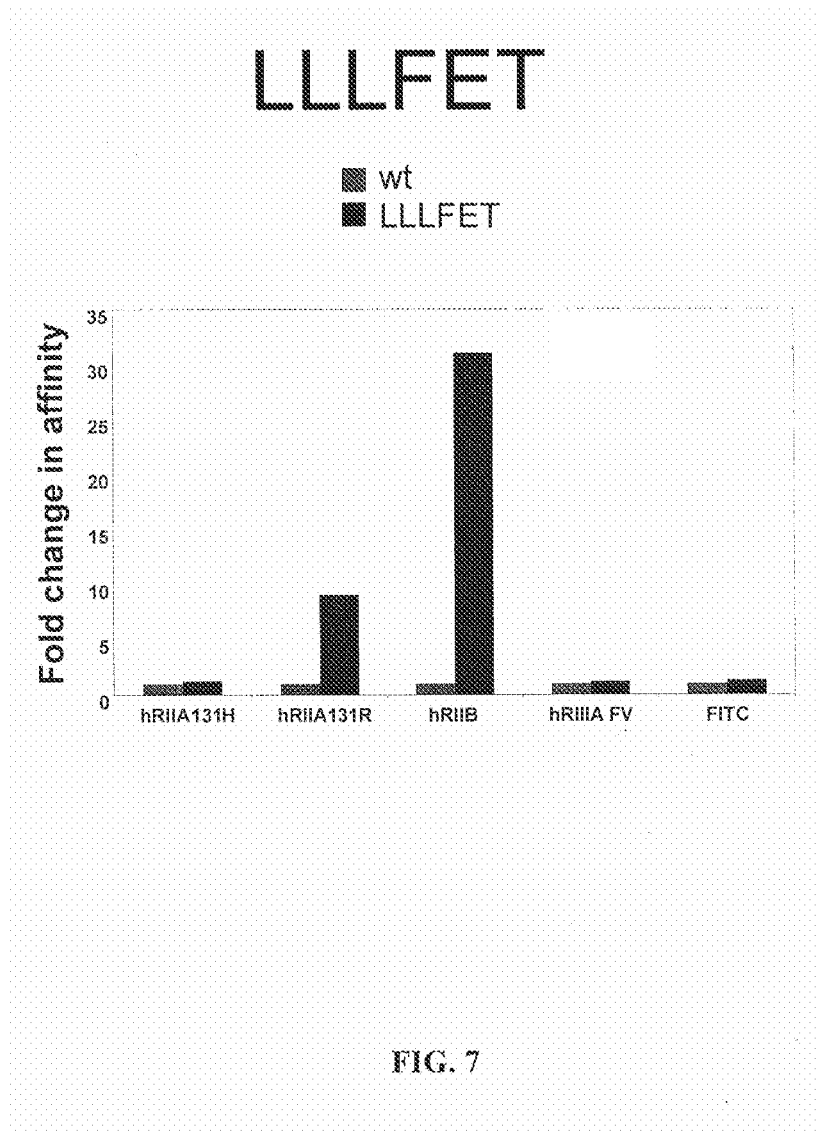
FIG. 7 illustrates the change in the affinity of the LLLFET variant [SEQ ID NO: 14] to the human FcγRIIB receptor.

The present invention provides an advantageous strategy for modifying the effector function of therapeutic antibodies, in mammals including humans. Disclosed are targets, methods, and reagents for specific activation and inhibition of Fc receptors in mammals including humans. Immunoglobulin G subclasses display significant differences in vivo in their ability to mediate effector responses, contributing to the variable activity of anti-microbial and anti-tumor antibodies and the pathogenic heterogeneity of autoantibodies. This differential activity results from the affinities of IgG subclasses for specific activating IgG Fc receptors as compared to their affinities for the inhibitory IgG Fc receptor. Applicants' invention is based on the discovery that in the human system, the in vivo activity of an antibody or variant thereof can be predicted by: determining a binding affinity of the antibody or variant thereof to an Fc activating receptor or receptors; determining a binding affinity of the antibody or variant thereof to a Fc inhibitory receptor, and calculating the ratio of said activating binding affinity to said inhibitory binding affinity (A/I ratio), wherein the magnitude of said ratio is an indication and predictive of the in vivo activity in vivo of the antibody or variant thereof. Activating receptors for the purposes of this calculation are selected from the group including FcRIIA, IIC or IIIA and the allelic variants of these receptors that are known to modify IgG binding. The high affinity FcRI is not included in these calculations. Thus, Applicants' invention provides a method of selecting a modified antibody for its in vivo based on determining its ratio of binding affinity to activating Fc receptors versus inhibitory Fc receptors and then selecting the modified antibody with the desired ratio of activating to inhibitory receptor affinity. These differential affinities result in antibodies with significantly different ratios of activation to inhibitory receptor binding that are predictive of the in vivo activity of a modified antibody and are important considerations in the design of therapeutic antibodies and vaccines. It can be appreciated that such modified antibodies can either activate or inhibit the activation of effector cells, such as macrophages, mast cells and dendritic cells. On lymphocytes, such as B cells, antibodies modified to preferentially engage the inhibitory FcRIIB receptor in conjunction with other activation receptors will effectively reverse the activation response and serve to reduce B cell activation.

To aid in the understanding of the invention, the following non-limiting definitions are provided:

DEFINITIONS

Throughout the present specification and claims, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), which is expressly incorporated herein by reference. The "EU index as in Kabat" refers to the residue numbering of the human IgG 1 EU antibody.

The term "native" or "parent" refers to an antibody comprising an amino acid sequence which lacks one or more of the Fc region modifications disclosed herein and which differs in effector function compared to a modified antibody as herein disclosed. The parent polypeptide may comprise a native sequence Fc region or an Fc region with pre-existing amino acid sequence modifications (such as additions, deletions and/or substitutions).

The term "Fc region" is used to define a C-terminal region of an immunoglobulin heavy chain. The "Fc region" may be a native sequence Fc region or a variant Fc region. The boundaries of the Fc region of an immunoglobulin heavy chain might vary. In some references, the human IgG heavy chain Fc region is defined to stretch from an amino acid residue at position Cys226, or from Pro230, to the carboxyl-terminus thereof. For the purposes of this invention, the term is defined as starting at amino acid 210 (as in Kabat) and ending at the carboxy terminus of the heavy chain.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, *Mol Immunol*, 22, 161-206 (1985), which is incorporated herein by reference).

The "CH3 domain" comprises the stretch of residues C-terminal to a CH2 domain in an Fc region (i.e., from about amino acid residue 341 to about amino acid residue 447 of an IgG).

The term "hinge region" is generally defined as stretching from Glu216 to Pro230 of human IgG1 (Burton (1985). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e., residues 233 to 239 of the Fc region. Prior to the present invention, FcγR binding was generally attributed to amino acid residues in the lower hinge region of an IgG Fc region.

The term "binding domain" refers to the region of a polypeptide that binds to another molecule. In the case of an FcR, the binding domain can comprise a portion of a polypeptide chain thereof (e.g., the α chain thereof) which is responsible for binding an Fc region. One useful binding domain is the extracellular domain of an FcR chain.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. Outside of the mutations specified herein, the variant Fc region herein will preferably possess at least about 80% homology with a native sequence Fc region and/or with an Fc region of a parent polypeptide, and most preferably at least about 90% homology therewith, more preferably at least about 95% homology therewith, even more preferably, at least about 99% homology therewith, or most preferably, 100% homology therewith.

The term "altered glycosylation" refers to an antibody, as defined above, be it native or modified, in which the carbohydrate addition to the heavy chain constant region is manipulated to either increase or decrease specific sugar components. For example, antibodies prepared in specific cell lines may be deficient in the attachment of sugar moieties such as fucose and sialic acid. Alternatively, antibodies can be isolated on specific lectin affinity reagents to enrich or deplete for specific sugar moieties. For example, the lectin isolated from *Sambuccus nigra* will bind sialic acid and permit the enrichment or depletion of antibodies with this specific sugar residue attached. Enzymatic treatment of antibodies may also enrich or deplete specific sugar residues such as neuraminidase treatment to remove sialic acid or sialytransferase to introduce sialic acid residues.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred human FcR is one which binds an IgG antibody (a gamma receptor) and includes receptors of the human FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, *Annu Rev Immunol*, 15, 203-234 (1997); FcRs are reviewed in Ravetch and Kinet, *Annu Rev Immunol*, 9, 457-92 (1991); Capel et al., *Immunomethods*, 4, 25-34 (1994); and de Haas et al., *J Lab Clin Med*, 126, 330-41 (1995), each of which is incorporated herein by reference).

"Antibody-dependent cell-mediated cytotoxicity" and "ADCC" refer to an in vitro or in vivo cell-mediated reaction in which nonspecific cytotoxic cells that express FcRs (e.g., monocytic cells such as natural killer (NK) cells and macrophages) recognize bound antibody on a target cell and subsequently cause lysis of the target cell. In principle, any effector cell with an activating FcγR can be triggered to mediate ADCC. One such cell the NK cell, express FcγRIII only, whereas monocytes, depending on their state of activation, localization, or differentiation, can express FcγRI, FcγRII, and FcγRIII FcR expression on hematopoietic cells is summarized in Ravetch and Bolland, *Annu Rev Immunol*, (2001), which is incorporated herein by reference.

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, and neutrophils, with PBMCs and NK cells being preferred. The effector cells may be isolated from a native source thereof, e.g., from blood or PBMCs as described herein.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments", as defined for the purpose of the present invention, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., Nature, 352, 624-628 (1991) and Marks et al., J Mol Biol, 222, 581-597 (1991), for example, each of which is incorporated herein by reference.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., Proc Natl Acad Sci USA, 81, 6851-6855 (1984); Neuberger et al., Nature, 312, 604-608 (1984); Takeda et al., Nature, 314, 452-454 (1985); International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., Nature, 321, 522-525 (1986); Riechmann et al., Nature, 332, 323-329 (1988); Presta, Curr Op Struct Biol, 2, 593-596 (1992); U.S. Pat. No. 5,225,539, each of which is incorporated herein by reference.

The term "immunoadhesin" refers to antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. In a preferred embodiment, the constant domain sequence is derived from an IgG, and includes Fc region thereof as described above.

The term "about" refers to a range of values which would not be considered by a person of ordinary skill in the art as substantially different from the baseline values. When this term is used in conjunction to binding affinity to Fc receptors, it refers to a range between 5-25% of the baseline values. When this term refers to the homology and/or similarity of the amino acid sequences, this term refers to the range within 10% of the baseline value.

Generation of Modified Antibodies

Modified antibodies include those in which specific amino acid substitutions, additions or deletions are introduced into a parental sequence through the use of recombinant DNA techniques to modify the genes encoding the heavy chain constant region. The introduction of these modifications follows well-established techniques of molecular biology, as described in manuals such as Molecular Cloning (Sambrook and Russel, (2001)). In addition, modified antibodies will include those antibodies which have been selected to contain specific carbohydrate modifications, obtained either by expression in cell lines known for their glycosylation specificity (Stanley P., et al., Glycobiology, 6, 695-9 (1996); Weikert S., et al., Nature Biotechnology, 17, 1116-1121 (1999); Andresen D C and Krummen L., Current Opinion in Biotechnology, 13, 117-123 (2002)) or by enrichment or depletion on specific lectins or by enzymatic treatment (Hirabayashi et al., J Chromatogr B Analyt Technol Biomed Life Sci, 771, 67-87 (2002); Robertson and Kennedy, Bioseparation, 6, 1-15 (1996)). It is known in the art that quality and extent of antibody glycosylation will differ depending on the cell type and culture condition employed. (For example, Patel et al., Biochem J, 285, 839-845 (1992)) have reported that the content of sialic acid in antibody linked sugar side chains differs significantly if antibodies were produced as ascites or in serum-free or serum containing culture media. Moreover, Kunkel et al., *Biotechnol Prog*, 16, 462-470 (2000) have shown that the use of different bioreactors for cell growth and the amount of dissolved oxygen in the medium influenced the amount of galactose and sialic acid in antibody linked sugar moieties. These studies, however, did not address how varying levels of sialic acid residues influence antibody activity in vivo.

Creation of Desialylated Antibodies.

Most of the carbohydrates on antibodies are N-linked at Asn297 in the CH2 domain. High percentages of the Fc-associated carbohydrates in humans, mice and from hybridomas are incompletely processed, varying in structure-type (complex- or high mannose-type), in the amounts of sialic acid, galactose and/or GlcNAc residues in the outer branches, and in core fucosylation. Only 12-15% of Fc-associated carbohydrates are sialylated. The level of antibody glycosylation and specifically galactosylation and sialylation might also vary significantly in human autoimmune disease. For example IgG antibodies in human rheumatoid arthritis have been found to contain decreased levels of galactose and sialic acid in antibody linked sugar moieties (Parekh R B, et al., *Nature*, 316, 452-457 (1985); Tsuchiya et al., *J. Immunol.*, 151, 1137-1146 (1993); Matsumoto et al., *J Biochem* (Tokyo), 128, 621-628 (2000); Rademacher et al., *Proc Natl Acad Sci USA*, 91, 6123-6127 (1994)) The antibodies of the present invention can be further purified or modified so that they have a decreased amount of sialic acid compared to unmodified and/or unpurified antibodies. Multiple methods exist to reach this objective. In one method, the source of the recombinantly expressed, antigen-specific antibody is passed through an affinity chromatography column containing a lectin, known to bind sialic acid. Lectin affinity chromatography is widely known in the art and is described in, for example, Schmauser at al., *Glycobiology*, 12, 1295-305 (1999). As a result of this technique, the sialylated portion of the antibodies will be retained in the column while desialylated portion will pass through. A person of ordinary skill in the art will appreciate that the affinity chromatography method described above can be used not only with recombinantly expressed antigen-specific antibodies, but with unspecific unpurified sources as well, such as, for example, intravenous immunoglobulin ("IVIG") preparations. We have observed that approximately 15-20% of IVIG is sialylated. Accordingly, this invention provides for antibodies with lower sialic acid content produced from IVIG and the method of production of such antibodies.

Further, one may employ an enzymatic reaction with sialidase, such as, for example, *Arthrobacter ureafacens* sialidase. The conditions of the reaction are generally described in the U.S. Pat. No. 5,831,077. Other non-limiting examples of suitable enzymes are neuraminidase and N-Glycosidase F, as described in Schloemer et al., *J. Virology*, 15(4), 882-893 (1975) and in Leibiger et al., *Biochem J.*, 338, 529-538 (1999), respectively. The desialylated antibodies may be further purified by using affinity chromatography, as described above.

Still further, if the starting material for the antibody samples comprises antibodies grown in cell culture, desialylation can be achieved by modifying culture media conditions. For example, decreasing the sialic acid content of the mature glycoprotein produced by mammalian cell culture can be achieved by increasing cell specific productivity of the cell culture. The cell specific productivity is increased by providing a cell culture which either contains about 6 mM to about 12 mM of an alkanoic acid or salt thereof or has the osmolality at about 450-600 mOsm/kg. This method is described in, e.g., U.S. Pat. No. 6,656,466.

Also, antibodies of interest may be expressed in cell lines having deficiency in sialylating these antibodies. Suitable examples of these cells are Lec 2 and Lec 3 mutants of CHO cells. (See for example, Stanley, Mol Cel Biol, 9(2), 377-383 (1989)). It has been shown that approximately 4% of glycoproteins, including antibodies grown in these cells are sialylated (Jassal et al., *Biochemical and Biophysical Research Communications*, 286, 243-249 (2001); Lund et al., *J Immunol*, 157(11), 4963-4969 (1996)).

A person of ordinary skill in the art will appreciate that different combinations of desialylation methods, disclosed above, can lead to production of antibodies with extremely low level of sialylation. For example, one can express antibodies in sialylation-deficient cell lines, such as Lec 2 and Lec 3, and then further enrich the desialylated fraction of these antibodies by, for example, desialylating the antibodies in an enzymatic reaction followed by affinity chromatography using lectin-containing columns. Similarly, an enzymatic reaction followed by affinity chromatography may be used for IVIG source of antibodies.

To examine the extent of glycosylation on these modified antibodies, the antibodies can be purified and analyzed in SDS-PAGE under reducing conditions. The heavy chains of the modified antibodies will migrate at faster rates, due to desialylation, compared to that of the parent antibody. From the relative migration rates of the peptides in SDS-PAGE, which are inversely proportional to the molecular sizes, the extent of glycosylation at the different sites can be estimated.

Assays

The A/I ratio of the modified antibody candidates of the present invention can be readily determined by any number of assays widely known in the art, such as for example, a competition or sandwich ELISA, a radioimmunoassay, a dot blot assay, a fluorescence polarization assay, a scintillation proximity assay, a homogeneous time resolved fluorescence assay, a resonant mirror biosensor analysis, and a surface plasmon resonance analysis.

Generally, in one embodiment, the modified antibody candidates, the activating Fc receptors, and/or inhibitory Fc receptors is directly labeled with a detectable label and may be detected directly. In another embodiment, neither the modified antibody candidates nor the activating Fc receptor nor inhibitory Fc receptor is labeled. Instead, a secondary antibody or other molecule that can bind the modified antibody candidates or one of the activating Fc receptor or the inhibitory Fc receptor is labeled. As is well known to one of skill in the art, a secondary antibody is chosen that is able to specifically bind the specific species and class of the modified antibody candidates or the activating or inhibitory Fc receptor. For example, if the modified antibody candidates are human IgGs, then the secondary antibody may be an anti-human-IgG. The amount of an antibody-receptor complex in the biological sample can be detected by detecting the presence of the labeled secondary antibody. Other molecules that can bind to antibodies include, without limitation, Protein A and Protein G, both of which are available commercially, for example, from Pierce Chemical Co. (Rockford, Ill.)

Suitable labels for the modified antibody candidates, the activating Fc receptor, the inhibitory Fc receptor or secondary antibody are widely known in the art and include various enzymes, prosthetic groups, fluorescent materials, luminescent materials, magnetic agents and radioactive materials. Examples of suitable enzymes include horseradish peroxidase, alkaline phosphatase, p-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; examples of a luminescent material include luminol luciferin, pyrogallol, or isoluminol; an example of a magnetic agent includes gadolinium; and examples of suitable radioactive material include $^{125}$I, $^{131}$I, $^{35}$S or $^{3}$H.

Competition ELISA.

Binding of modified antibody candidates to Fc activating and Fc inhibitory receptors can be measured by a competition ELISA. In this method, it would be advantageous to use an antibody with known A/I ratios as a control substrate for reaction with either the activating Fc receptors or the inhibitory Fc receptors, which are labeled, and use the modified antibody candidates as competitors. In another embodiment, the activating and the inhibitory Fc receptors would be unlabeled and a labeled secondary antibody against either the activating Fc receptor or the inhibitory Fc receptor may be added to the reaction in the second step.

Alternatively, one may use the modified antibody candidates as a substrate and use both the activating Fc receptors and the inhibitory Fc receptors as competitors. The activating receptor and the inhibitory Fc receptors may be labeled as discussed above. In yet another embodiment of this method, a labeled secondary antibody against either the activating Fc receptor or the inhibitory Fc receptor may be added to the reaction in the second step.

Sandwich ELISA.

In a Sandwich ELISA, the activating or the inhibitory Fc receptor is immobilized on a solid carrier and is brought into contact with a liquid containing the modified antibody candidates. Then the quantity of the bound modified antibody candidates is determined by adding a second antibody which is labeled with a detectable label such as a radioactive atom, a fluorescent or luminescent group or, in particular, an enzyme (for example horseradish peroxidase (HRP)). If the modified antibody candidates are human IgGs, then the second antibody may be an anti-human-IgG antibody. The amount of the bound second antibody is then determined by measuring the activity, for example the enzyme activity of the label. This activity is a measure of binding of the modified antibody candidates to the activating Fc receptor or the inhibitory Fc receptor.

Alternatively, the modified antibody candidates may be immobilized and a mixture containing the activating Fc receptor or the inhibitory Fc receptor added to the modified antibody candidates. In this embodiment, the secondary antibody would be used against the activating Fc receptor or the inhibitory Fc receptor.

It is important that the secondary antibody binds an epitope of its target, which is not affected by binding of the modified antibody candidates to the activating or the inhibitory Fc receptor.

Radioimmunoassay.

A radioimmunoassay can also be used in determining binding affinities of the modified antibody candidates to activating Fc receptors and inhibitory Fc receptors. In the first step of this method, radioactively-labeled modified antibody candidates are mixed with the activating or the inhibitory Fc receptors. The antibodies may be labeled by, for example, radioactive iodine attached to tyrosine moieties. In the second step, non-labeled modified antibody candidates are added to the mix in the known quantities and antigen-antibody complexes are removed from the mixture by, for example, precipitation. The amount of labeled unbound modified antibody candidates is then determined.

Dot Blot Analysis.

A dot blot procedure can also be used for this analysis. The use of the dot blot procedure eliminates the need to perform electrophoresis and allows rapid analysis of a large number of samples. In one embodiment of this method, different dilutions of the activating Fc receptors or the inhibitory Fc receptors can be placed on a membrane, such as, for example, nitrocellulose membrane, and contacted with radioactively or fluorescence labeled modified antibody candidates.

A person skilled in the art will appreciate that the modified antibody candidates do not have to be labeled. In that case, after incubating the membrane-bound activating or inhibitory Fc receptor with the modified antibody candidates, a secondary antibody, which is labeled, is added to the reaction. The amount of signal produced by the label (radioactivity, light, color, etc) can then be quantified.

Fluorescence Polarization Assay.

This assay is based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component, such as an antibody with a relatively lower rate of rotation, will retain a relatively greater degree of polarization of emitted light than if in free solution. Thus, a person of skill in the art can label the activating Fc receptor or the inhibitory Fc receptor with an appropriate label and contact the labeled receptor with the modified antibody candidates. The fluorescence polarization assays can be conducted in commercially available automated instruments such as IMx®, TDx®, and TDxFLx™. (Abbott Laboratories, Abbott Park, Ill.).

Scintillation Proximity Assay.

The activating Fc receptor or the inhibitory Fc receptor can be coupled to a scintillation-filled bead. Binding of radiolabeled modified antibody candidates to the activating Fc receptors or the inhibitory Fc receptors would result in emitted light which can be quantified on a scintillation counter. Commercial kits for the scintillation proximity assay are currently available and may be purchased from, for example, Amersham Life Science (Piscataway, N.J.).

Homogeneous Specific Binding Assay.

In this assay, a conjugate is formed between a binding substance (i.e. the modified antibody candidates or the activating or inhibitory Fc receptor) and coupled to a label, which is chosen in such a way that it behaves differently depending on whether the binding substance is bound or free. Thus, in one embodiment of the method, different samples containing known amounts of labeled activated Fc receptors or labeled inhibitory Fc receptor in a liquid medium can be contacted with a solid matrix coated with or impregnated with the modified antibody candidates. In another embodiment, the activating Fc receptor or the inhibitory Fc receptor can be placed onto a solid carrier and contacted with different liquid samples containing known amounts of the modified antibody candidates which are labeled. Examples of labels suitable for this method are chemiluminescent compounds and enzymes, as disclosed above. Change in chemiluminescence can be measured, thus reflecting on the relative amount of bound modified antibody candidates.

Surface Plasmon Resonance Analysis.

This method is based on quantifying the intensity of electromagnetic waves, also called surface plasmon waves, which may exist at the boundary between a metal and a dielectric.

Such waves can be exited by light which has its electric field polarized parallel to the incident plane (i.e., transverse magnetic (TM) polarized).

In this method, one of the reagents (i.e., the modified antibody candidates or the activating Fc receptor or the inhibitory Fc receptor) is coupled to the dextran layer (covering the metal film) of a sensor chip and solutions containing different concentrations of the other reagent (i.e. the activating Fc receptor or the inhibitory receptor or the antibody, respectively) are allowed to flow across the chip. Binding (association and dissociation) is monitored with mass sensitive detection. BIACORE® (Biacore AB, Uppsala, Sweden) equipment can be used for this method. The application of this method to the present invention is described in detail in Example 1 of the disclosure.

Other modifications of these assays, not disclosed in this application will be apparent to a person of ordinary skill in the art. The claims of the present invention include all such modifications.

Therapeutic Formulations

Therapeutic formulations of the modified antibody can be prepared for storage by mixing the modified antibody having the desired degree of purity with optional physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may also be prepared. Suitable examples of sustained-release preparations include semipermeable matrices of solid hydrophobic polymers containing the modified antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (see, e.g., U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

EXAMPLES

Specific embodiments of the present invention will now be described. The examples are illustrative only, and are not intended to limit the remainder of the disclosure in any way.

Example 1

FC Variant Selection

To identify IgG1 Fc variants with preferential binding affinity to the inhibitory FcRIIB receptor, a library of Fc variants was constructed according to published methods. (Boder et al, *Yeast surface display for screening combinatorial polypeptide libraries*, Nature Biotechnology, 15:553-557, April 1997; Chao et al, *Isolating and engineering human antibodies using yeast surface display*, Nature Protocols, 1:755-768, 2006).

Library Construction.

Libraries were constructed by homologous recombination of a mutated hIgG1 heavy-chain constant-region insert into the pYD1 (Invitrogen) yeast-secretion vector template according to previously published methods (Chao et al, *Nat Protoc* 1:755-768 (2006)). The $hIgG_1$ CH1 to CH3 constant domain gene inserts were transformed with digested template vector by electroporation into the yeast strain EBY100 (Invitrogen).

Library Construction: Preparation of Digested Template Vector and Mutagenic Gene Inserts.

The pYD1 heavy-chain template vector was prepared by digestion with EcoRI (Fermentas) and XhoI (Fermentas), which flank the 5' region of the hIgG1 CH1 domain (EcoRI) and 3' region of the CH3 domain (XhoI). To introduce the EcoRI and XhoI restriction endonulcease sites flanking the hIgG1 CH1-CH3 domains, PCR amplification from the pCI-4-4-20 template was performed using the primers FcFw (SEQ ID NO: 2) and IgG1re (SEQ ID NO: 3) (all Oligos from Operon). For library generation random mutagenesis of CH1-CH3 was performed by error prone PCR (Genemorph II kit, Stratagene) with oligonucleotides Y1fw (SEQ ID NO: 4) and Y1re (SEQ ID NO: 5). Three libraries were constructed with conditions set to obtain 1-3, 3-8 or 8-15 mutations per DNA copy, respectively. The 3 libraries were combined and the resulting library had ≈2×10$^7$ transformants, and was amplified using oligonucleotides Y1fw (SEQ ID NO: 4) and Y1re (SEQ ID NO: 5) under standard PCR conditions with 250 base pairs of overlap with the digested template vector for efficient yeast homologous recombination.

Oligonucleotides.

Oligonucleotides are as follows:

FcFw (5'-AATTGAATTCGCCTCCACCAAGGGCCC-3') (SEQ ID NO: 2)

IgG1re (5'-AATTCTCGAGTCATTTACCCGGAGA-CAGGG-3') (SEQ ID NO: 3)

Y1fw (5'-ATCTGTACGACGATGACGATAAGGTAC-CAGGATCCAGTGTGGTGGAATTC-3') (SEQ ID NO: 4)

Y1re (5'-AGAGGGTTAGGGATAGGCTTACCTTC-GAAGGGCCCTCTAGACTCGAGTCA-3') (SEQ ID NO: 5)

Igfw (5'-CACCAAGGGCCCATCGGTC-3') (SEQ ID NO: 6)

Igre (5'-AATTGAATTCTCATTTACCCGGAGA-CAGGG-3') (SEQ ID NO: 7)

Library Screening.

Library screening was performed using the cell-surface display assay (Boder et al, *Yeast surface display for screening combinatorial polypeptide libraries*, Natur Biotechnology, 15:553-557, April 1997). Briefly, libraries were grown in SD-CAA (2% glucose, 0.67% yeast nitrogen base, 0.54% Na$_2$HPO$_4$, 086% NaH$_2$PO$_4$H$_2$O, 0.5% casein amino acids) at 30° C. to an OD$_{600}$ of ≈5, and then induced in SG-CAA (2% galactose, 0.67% yeast nitrogen base, 0.54% Na$_2$HPO$_4$, 086% NaH$_2$PO$_4$H$_2$O, 0.5% casein amino acids) for 24 h at 20° C. Following this induction phase, yeast cells were washed twice with PBS containing 0.1% (w/vol) BSA (PBS/BSA) and 10$^{10}$ cells were labeled with biotinylated hFcγRIIB pre-loaded onto streptavidin-PE (BD Biosciences). The library was sorted for PE-positive cells on a BD FACSAria (Becton Dickinson) and the collected cells were restained with biotinylated hFcγRIIA$^{131R}$ pre-loaded onto streptavidin-APC (BD Biosciences). The library was sorted for APC-negative cells on a BD FACSAria (Becton Dickinson) and the collected cells were grown in SD-CAA supplemented with penicillin/streptomycin (Invitrogen), for a total of four rounds of screening. All clones isolated from screening were re-transformed into *E. coli* strain Top10 bacteria (Invitrogen), plasmids were purified and the CH1-CH3 domains were cloned into the pCI-4-4-20 hIgG1 template plasmid by PCR amplification with oligonucleotides Igfw (SEQ ID NO: 6) and Igre (SEQ ID NO: 7), and the restriction endonucleases ApaI and EcoRI.

Site Directed Mutagenesis.

For introduction of single point mutations into the 4-4-20 hIgG1 plasmid, mutagenesis of the 4-4-20 heavy-chain vector was performed using the Quikchange II Site-Directed Mutagenesis Kit (Stratagene). All point mutants were constructed by PCR amplification of the entire vector, using complementary primers containing the desired point mutations. Clones were identified and confirmed by subsequent sequencing and resequencing.

Characterization of Fc Mutants.

Plasmids encoding the 4-4-20 Fc mutants were co-transfected with the plasmid encoding the 4-4-20 antibody kappa-light chain into HEK293T cells. Cell culture supernatants were harvested and antibodies were purified by a sequence of ammoniumsulfate precipitation, protein affinity purification and size exclusion chromatography. The obtained antibodies were analyzed be SDS-PAGE under reducing and non-reducing conditions, lectin blot, surface plasmon resonance analysis and immune complex binding assays on CHO cells expressing human Fcγ-receptors hFcγRIIA$^{131H}$, CHO-hFcγRIIA$^{131R}$, or hFcγRIIB.

Mice.

γ$^{-/-}$FcγRIIB$^{-/-}$mice were generated in the Ravetch laboratory, backcrossed for 12 generations to the C57BL/6 background, and crossed to hFcγRIIAtg mice (The Jackson Laboratory). Female mice at 2 to 4 months of age were used for the experiments and maintained at the Rockefeller University animal facility. All experiments were performed in compliance with federal laws and institutional guidelines and have been approved by the Rockefeller University.

Cell Culture.

HEK293T and CHO cells were cultured according to the American Type Culture Collection guidelines. Recombinant cell lines CHO-hFcγRIIA$^{131H}$, CHO-hFcγRIIA$^{131R}$, and CHO-hFcγRIIB were generated by stable transfection with plasmids encoding hFcγRIIA$^{131H}$, hFcγRIIA$^{131R}$, or hFcγRIIB, respectively, and subsequent selection with 1-mg/ml geneticin (Invitrogen).

Antibodies and Recombinant Proteins.

The 4-4-20-human Fc chimeric variants and soluble hFcγ-receptors were produced by transient transfection of 293T cells and subsequent purification from culture supernants. For protein production, cells were cultured in DMEM (Invitrogen) supplemented with 1% Nutridoma SP (Roche). Cell culture supernatants were harvested 6 days after transfection, and protein was precipitated by ammonium sulfate precipitation. The 4-4-20 human Fc chimeric variants were produced by transient transfection of 293T cells and subsequent purification from cell-culture supernatants. For protein production, cells were cultured in DMEM (Invitrogen) supplemented with 1% Nutridoma SP (Roche). Recombinant receptors were purified with Ni-NTA (Qiagen) and recombinant antibodies were purified with protein G Sepharose (GE Healthcare) by affinity chromatography. All proteins were dialyzed against PBS. Purity was assessed by SDS/PAGE followed by Coomassie Blue staining.

Immune Complex Binding Assay.

Figure 8:
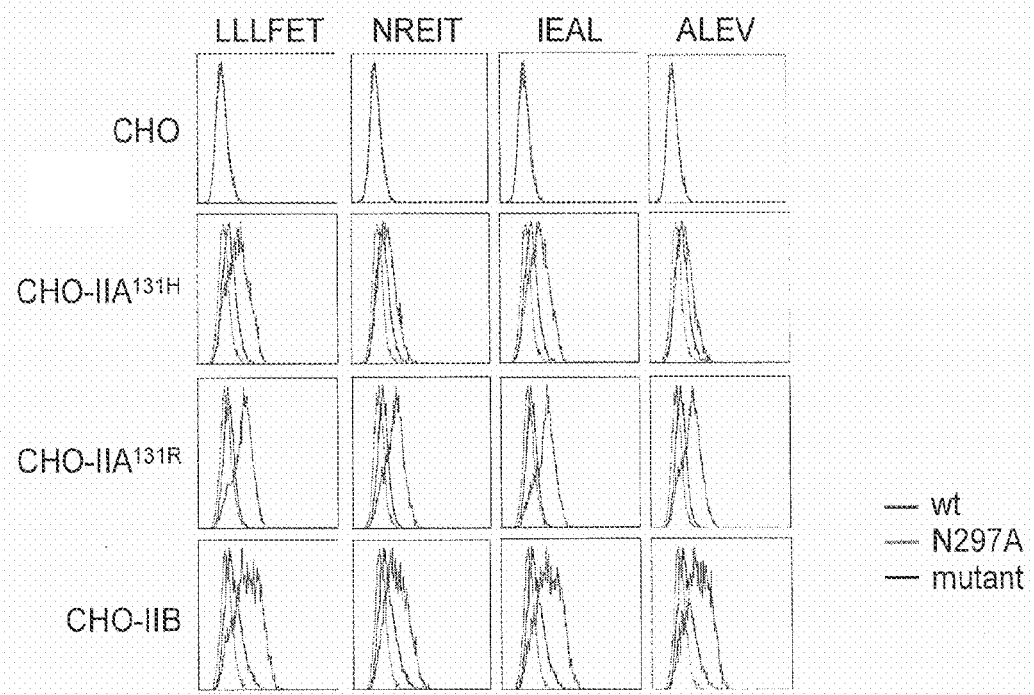
FIG. 8 illustrates the binding of four Fc variants to CHO cells expressing human activation or inhibitory FcRs as immune complexes as compared to wild type IgG1 Fc or an aglycosylated Fc variant lacking binding to all FcRs (N297A).

For studying immune complex binding to surface FcγRs, ICs were generated by incubating 10 μg of the respective 4-4-20 (anti-FITC) chimera with 10 μg of BSA-FITC (Sigma) in 1-ml PBS for 2 h at 37° C. while shaking gently. CHO cells were stained for 2 h at 4° C. with 1 μg, 0.5 μg, 0.2 μg, or 0.1 μg of ICs, washed with PBS and analyzed by FACS analysis. The result of such immune complex binding assay is depicted in FIG. 8.

Surface Plasmon Resonance Analysis.

To determine the interaction between soluble hFcγ-receptors RIa (R&D Systems), FcγRIIA$^{131H}$, FcγRIIA$^{131R}$, and FcγRIIB, FcγRIIA, Clq (Calbiochem), and 4-4-20 antibody chimera, steady-state affinity measurements on a Biacore T100 biosensor were performed. Antibodies were immobilized at high densities to CM5 sensor chips (Biacore) by standard amine coupling. Soluble hFcγ-receptors were injected in five different concentrations through flow cells at room temperature in HBS-EP running buffer (Biacore) for 3 min at a flow rate of 30 μl/min and dissociation was observed for 10 min. K$_d$ values were calculated after subtraction of background binding to a control flow cell using Biacore T100 Evaluation software. FIG. 1-7 show representative results of Biacore analysis.

Lectin Blot.

10 μg of 4-4-20 antibody chimera were resolved by SDS/PAGE using a polyacrylamide gel (NuPAGE, Invitrogen)

under nonreducing conditions. Proteins were transferred to a PVDF membrane (Millipore), blocked with Western Blocking Reagent (Roche), and followed by incubation with biotinylated LCA lectin (2 μg/ml, Vector Laboratories) and alkaline phosphatase-conjugated goat antibiotin antibody (Sigma). Bound antibody was visualized with 4-nitro blue tetrazolium chloride/5-bromo-4-chloro-3-indolyl phosphate (Roche).

Example 2

Mutants with Enhanced Affinity for hRIIB

Fc variants were obtained from the constructs of Example 1 that show enhanced binding to constructed FcγRIIB over FcγRIIA$^{131H}$, FcγRIIA$^{131R}$ and FcγRIIIA$^{158F}$. A number of promising Fc variants with optimized properties were obtained from the FcγRIIA, FcγRIIIA and FcγRIIB screen. Table 1 provides Fc variants that bind more tightly to FcγRIIIA, and thus are candidates for improving the effector function of antibodies and Fc fusions. These include a number of variants that comprise mutations at 215, 326, 359, and 396; 247, 252, 266, 278, 302, and 354; and 211, 243, 326, and 399. For example, variant "ZEAL" (ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKRIEPKSCD KTHTCPPCPAPELLG GPSVFLFPPKPKDTLMISRTPEVTCVVVDVSHEDPEVKFNWYVDGVEVHNAKTKPREE QYNSTYRVVSVLTVLHQDWLNGKEYKCKVSN EALPAPIEKTISKAKGQPREPQVYTLPP SRDEL AKNQVSLTCLVKGFYPSDIAVEWESNGQPENNYKTTP LVLDSDGSFFLYSKLTV DKSRWQQGNVFSCSVMHEALHNHYTQKSLSLSPGK, SEQ ID NO: 12) obtained from the constructs of Example 1 comprises the following four mutations: V215I, K326E, T359A, and P396L (underlined). Fc mutant "ALEV" (ASTKGPSVFPLAPSSKSTSGGTAALGCLVKDYFPEPVTVSWNSGALTSGVHTFPAVLQS SGLYSLSSVVTVPSSSLGTQTYICNVNHKPSNTK ADKRVEPKSCDKTHTCPPCPAPELLG GPSVFL LPPKPKDTLMISRTPEVTCVVVDVSHEDPEVKFNWY VDGVEVHNAKTKPREE QYNSTYRVVSVLTVLHQDWLNGKEYKCKVSN EALPAPIEKTISKAKGQPREPQVYTLPP SRDELTKNQVSLTCLVKGFYPSDIAVEWESNGQPENNYKTTPPVL VSDGSFFLYSKLTV DKSRWQQGNVFSCSVMHEALHNHYTQKSLSLSPGK, SEQ ID NO: 13) comprises the following four mutations: V211A, F243L, K326E, and D399V in SEQ ID NO: 1. Fc mutant "LLLFET" (ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKRVEPKSCD KTHTCPPC PAPELLGGPSVFLFPPKLKDTL LISRTPEVTCVVVDLSHEDPEVKFNWFVDG EEVHNAKT KPREEQYNSTYRVVSVLTVLHQDWLNGKEYKCKVSNKALPAPIEKTISKAKGQPREPQ VYTLPP TRDELTKNQVSLTCLVKGFYPSDIAVEWESNGQPEN NYKTTPPVLDSDGSFFL YSKLTVDKSRWQQGNVFSCSVMHEALHNHYTQKSLSLSPGK, SEQ ID NO: 14) comprises the following six mutations: P247L, M252L, V266L, Y278F, V302E, and S354T. Fc mutant "NREIT" (ASTKGPSVFPLAPSSKSTSGGTAALGCLVKDYFPEPVTVSWNSGALTSGVHTFPAVLQS SGLYSLSSVVTVPSSSLGTQTYICNVNHKPSNT NVDKRVEPKSCDKTHTCPPCPAPELLG GPSVFLFPPKPKDTLMISRTPEVTCVVVDVSHEDPEVKFNWYVDGVEVRNAKTKPREE QYNSTYRVVSVLTVLHQDWLNGKEYKCKVSN EALPAPIEKTISKAKGQPREPQVYTLPP SRDELTKNQVSLTCLIKGFYPSDI TVEWESNGQPENNYKTTPPVLDSDGSFFLYSKLTVD KSRWQQGNVFSCSVMHEALHNHYTQKSLSLSPGK, SEQ ID NO: 15) comprises the following mutations: K210N, H285R, K326E, V369I, A378T.

TABLE 1

| Mutant | hRI | hRIIA131H | hRIIA131R | hRIIB | hRIIIA FF | hRIIIA FV | C1q | FITC | A/I ratio | A/I ratio IIA131H/ IIB | A/I ratio IIA131R/ IIB |
|---|---|---|---|---|---|---|---|---|---|---|---|
| Affinities in KD (M): | | | | | | | | | | | |
| V215I-K326E-T359A-P396L [SEQ ID NO: 12] | | 4.79E−06 | 3.72E−07 | 3.21E−06 | 6.90E−06 | 4.89E−07 | 1.37E−07 | 2.39E−08 | 6.6 | 0.7 | 8.6 |
| K326E-A229T [SEQ ID NO: 16] | | 3.18E−06 | 5.48E−07 | 2.63E−06 | | 5.28E−07 | 1.29E−07 | 2.49E−08 | 5.0 | 0.8 | 4.8 |
| P247L-M252L-V266L-Y278F-V302E-5354T [SEQ ID NO: 14] | | 3.40E−06 | 5.23E−07 | 7.85E−07 | | 3.07E−06 | | 2.55E−08 | 0.3 | 0.2 | 1.5 |
| V211A-F243L-K326E-D399V [SEQ ID NO: 13] | | 7.16E−06 | 7.78E−07 | 6.12E−06 | | 3.43E−06 | | 2.07E−08 | 1.8 | 0.9 | 7.9 |
| P171S-S191C-G236A-K274M-T394P [SEQ ID NO: 17] | 1.18E−08 | 5.13E−07 | 4.73E−07 | 8.09E−06 | 1.10E−05 | 5.57E−06 | 5.59E−07 | 2.41E−08 | 1.5 | 15.8 | 17.1 |
| V188E-G236A-P244H-H268Y [SEQ ID NO: 18] | 1.74E−08 | 4.54E−07 | 3.94E−07 | 1.05E−05 | 1.40E−05 | 5.50E−06 | 4.05E−07 | 2.96E−08 | 1.9 | 23.0 | 26.5 |
| K205E-V211A-G237V-F243L-V273I-T366S-M428L [SEQ ID NO: 19] | 4.36E−08 | 1.00E−05 | 8.51E−07 | 1.34E−05 | 1.16E−05 | 8.99E−06 | 2.92E−07 | 2.55E−08 | 1.5 | 1.3 | 15.7 |

TABLE 1-continued

| Mutant | hRI | hRIIA131H | hRIIA131R | hRIIB | hRIIIA FF | hRIIIA FV | C1q | FITC | A/I ratio | A/I ratio IIA131H/IIB | A/I ratio IIA131R/IIB |
|---|---|---|---|---|---|---|---|---|---|---|---|
| G236A-F243I-I332T [SEQ ID NO: 20] | 4.23E−08 | 4.82E−07 | 9.44E−07 | 1.67E−05 | 1.12E−05 | 7.04E−06 | 2.57E−08 | 1.62E−08 | 2.4 | 34.7 | 17.7 |
| L163P-S183G-K222E-G236A-N276D-S298G-D312G [SEQ ID NO: 21] | 6.66E−08 | 1.06E−06 | 4.79E−07 | 1.40E−05 | 1.58E−05 | 9.32E−06 | 3.92E−07 | 2.13E−08 | 1.5 | 13.3 | 29.3 |
| G236A-K246E-F372Y-T394A-Q419L [SEQ ID NO: 22] | 3.61E−08 | 4.67E−07 | 4.98E−07 | 9.80E−06 | 1.19E−05 | 6.76E−06 | 7.03E−07 | 2.73E−08 | 1.4 | 21.0 | 19.7 |
| L163P-S183G-K222E-G236A-N276D-S298G-T299A-D312G [SEQ ID NO: 23] | | 1.34E−06 | 7.81E−07 | 8.48E−06 | | | | | | 6.3 | 10.9 |
| G236A-F243I-S298G-T299A-I332T [SEQ ID NO: 24] | | 4.63E−07 | 3.12E−07 | 5.34E−06 | | | | | | 11.6 | 17.1 |
| F243I [SEQ ID NO: 25] | | 5.60E−06 | 7.72E−06 | 1.18E−05 | 9.93E−06 | 7.05E−06 | 9.55E−08 | | 1.7 | 2.1 | 1.5 |
| I332T [SEQ ID NO: 26] | | 9.03E−07 | 6.37E−06 | 8.54E−06 | 1.06E−05 | 2.61E−06 | 3.55E−08 | | 3.3 | 9.5 | 1.3 |
| S239D [SEQ ID NO: 27] | | 1.46E−06 | 1.48E−06 | | 1.69E−06 | 3.07E−07 | 2.48E−07 | | | | |
| K326E [SEQ ID NO: 28] | | 1.34E−06 | 8.38E−07 | | 7.25E−06 | 5.67E−07 | 6.33E−08 | | | | |
| T394P [SEQ ID NO: 29] | | 5.94E−06 | 8.70E−06 | 1.08E−05 | | | | | | 1.8 | 1.2 |
| P396L [SEQ ID NO: 30] | | 7.66E−07 | 4.88E−06 | 6.04E−06 | | | | | | 7.9 | 1.2 |
| S298G [SEQ ID NO: 31] | | 1.29E−05 | 1.06E−05 | | | | | | | | |
| S298G-T299A [SEQ ID NO: 32] | | 7.00E−06 | 1.69E−06 | 5.68E−06 | n.b. | n.b. | n.b. | | | 0.8 | 3.4 |
| Fold change in affinity | | | | | | | | | | | |
| V215I-K326E-T359A-P396L [SEQ ID NO: 12] | 0.9 | 12.8 | 7.6 | 2.2 | 7.2 | 2.1 | 1.4 | 1.1 | 0.7 | 8.6 | |
| K326E-A339T [SEQ ID NO: 16] | 1.4 | 8.7 | 9.3 | | 6.7 | 3.8 | 1.4 | 1.4 | 0.8 | 4.8 | |
| P247L-M252L-V266L-Y278F-V302E-S354T [SEQ ID NO: 14] | 1.3 | 9.1 | 31.0 | | 1.2 | | 1.3 | 27.0 | 0.2 | 1.5 | |
| V211A-F243L-K326E-D399V [SEQ ID NO: 13] | 0.6 | 6.1 | 4.0 | | 1.0 | | 1.6 | 3.9 | 0.9 | 7.9 | |
| P171S-S191C-G236A-K274M-T394P [SEQ ID NO: 17] | 1.1 | 8.4 | 10.1 | 3.0 | 1.2 | 0.3 | 0.5 | 0.6 | 12.0 | 15.8 | 17.1 |
| V188E-G236A-P244H-H268Y [SEQ ID NO: 18] | 0.7 | 9.5 | 12.1 | 2.3 | 0.9 | 0.3 | 0.7 | 0.4 | 9.2 | 23.0 | 26.5 |
| K205E-V211A-G237V-F243L-V273I-T366S-M428L [SEQ ID NO: 19] | 0.4 | 0.4 | 5.6 | 1.8 | 1.2 | 0.4 | 0.7 | 0.7 | 4.2 | 1.3 | 15.7 |
| G236A-F243I-I332T [SEQ ID NO: 20] | 0.4 | 8.9 | 5.0 | 1.5 | 1.2 | 0.5 | 0.8 | 1.1 | 2.7 | 34.7 | 17.7 |
| L163P-S183G-K222E-G236A-N276D-S298G-D312G [SEQ ID NO: 21] | 0.4 | 4.1 | 9.9 | 1.7 | 0.8 | 0.5 | 0.7 | 1.0 | 3.7 | 13.3 | 29.3 |
| G236A-K246E-F372Y-T394A-Q419L [SEQ ID NO: 22] | 0.7 | 9.2 | 9.6 | 2.5 | 1.1 | 0.6 | 0.4 | 0.8 | 3.9 | 21.0 | 19.7 |

TABLE 1-continued

| Mutant | hRI | hRIIA131H | hRIIA131R | hRIIB | hRIIIA FF | hRIIIA FV | C1q | FITC | A/I ratio | A/I ratio IIA131H/ IIB | A/I ratio IIA131R/ IIB |
|---|---|---|---|---|---|---|---|---|---|---|---|
| L163P-S183G-K222E-G236A-N276D-S298G-T299A-D312G [SEQ ID NO: 23] | | 2.6 | 7.4 | 1.3 | | | | | | 6.3 | 10.9 |
| G236A-F243I-S298G-T299A-I332T [SEQ ID NO: 24] | | 7.4 | 18.5 | 2.0 | | | | | | 11.6 | 17.1 |
| F243I [SEQ ID NO: 25] | 0.6 | 0.9 | 0.9 | 1.4 | 0.4 | 0.7 | | | 2.1 | 2.1 | 1.5 |
| I332T [SEQ ID NO: 26] | 4.0 | 1.1 | 1.2 | 1.3 | 1.1 | 1.8 | | | 1.1 | 9.5 | 1.3 |
| S239D [SEQ ID NO: 27] | 2.3 | 4.9 | 4.3 | 7.4 | 5.3 | 0.6 | | | | | 0.0 |
| K326E [SEQ ID NO: 28] | 2.5 | 8.7 | 3.5 | 1.7 | 2.9 | 2.2 | | | | | 0.0 |
| T394P [SEQ ID NO: 29] | 0.5 | 1.0 | 1.1 | | | | | | | 1.8 | 1.2 |
| P396L [SEQ ID NO: 30] | 4.0 | 1.8 | 2.0 | | | | | | | 7.9 | 1.2 |
| S298G [SEQ ID NO: 31] | 0.3 | 0.6 | | | | | | | | | 0.0 |
| S298G-T299A [SEQ ID NO: 32] | 0.8 | 3.0 | 1.7 | | | | | | | 0.8 | 3.4 |

A generic heavy chain of IgG1 is illustrated as SEQ ID NO:1 below. Since this invention is related most closely to the Fc fragment which is located in the carboxy portion of IgG heavy chain, the first 117 amino acids are generically designated as "X" and may represent portions suitable for an antibody specific for an antigen of choice. The numbering of the residue in the portion of SEQ ID NO: 1 corresponding to amino acids 118 through 447 follows Kabat numbering.

XXXXXXXXXX$^{10}$ XXXXXXXXXX$^{20}$ XXXXXXXXXX$^{30}$ XXXXXXXXXX$^{40}$ XXXXXXXXXX$^{50}$ XXXXXXXXXX$^{60}$ XXXXXXXXXX$^{70}$ XXXXXXXXXX$^{80}$ XXXXXXXXXX$^{90}$ XXXXXXXXXX$^{100}$ XXXXXXXXXX$^{110}$ XXXXXXX$^{117}$ $^{118}$AST$^{120}$ KGPSVF-PLAP$^{130}$ SSKSTSGGTA$^{140}$ ALGCLVKDYF$^{150}$ PEP-VTVSWNS$^{160}$ GALTSGVHTF$^{170}$ PAVLQSSGLY$^{180}$ SLSS-VVTVPS$^{190}$ SSLGTQTYIC$^{200}$ NVNHKPSNTK$^{210}$ VDKRVEPKSC$^{220}$ DKTHTCPPCP$^{230}$ APELLGGPSV$^{240}$ FLFPPKPKDT$^{250}$ LMISRTPEVT$^{260}$ CVVVDVSHED$^{270}$ PEVKFNWYVD$^{280}$ GVEVHNAKTK$^{290}$ PREEQYN-STY$^{300}$ RVVSVLTVLH$^{310}$ QDWLNGKEYK$^{320}$ CKVSNKALPA$^{330}$ PIEKTISKAK$^{340}$ GQPREPQVYT$^{350}$ LPPSRDELTK$^{360}$ NQVSLTCLVK$^{370}$ GFYPSDIAVE$^{380}$ WESNGQPENN$^{390}$ YKTTPPVLDS$^{400}$ DGSFFLYSKL$^{410}$ TVDKSRWQQG$^{420}$ NVFSCSVMHE$^{430}$ ALH-NHYTQKS$^{440}$ LSLSPGK$^{447}$ (SEQ ID NO: 1).

The generic human IgG1 heavy chain sequence (SEQ ID NO:1) showing positions relevant to the design of the Fc variant experimental library. The sequence includes the hinge region, domain Cγ2, and domain Cγ3. Residue numbers are according to the EU index as in Kabat. Positions relevant to the experimental library are underlined. Because of observed polymorphic mutations at a number of Fc positions, slight differences between the presented sequence and sequences in the literature may exist.

Example 3

The present invention provides a mechanistic basis for the observed variation in IgG subclass activity in both active and passive vaccination and in the variable pathogenicity of the IgG subclasses in autoimmune conditions. The selective FcγR binding affinities of the IgG subclasses, and not their ability to fix complement, is predictive of the in vivo activity for cytotoxic antibodies in models of tumor clearance, platelet and B cell depletion (Uchida et al., *J Exp Med* 199, 1659-69. (2004); Clynes and Ravetch (1995); Clynes (1998); Samuelsson (2001)). Similarly, the biological consequences of modifications to IgG antibodies are, in turn, dependent on their effects on specific FcR binding affinities that result in changes to the ratio of activation to inhibitory receptor affinities. These considerations will be significant factors in the design of both antibody-based immunotherapeutics and active vaccination protocols to insure either the selective engineering of IgG Fc domains or induction of IgG subclasses with optimal FcγR activation to inhibitory ratios.

To test the role of Fc variants with enhanced binding to FcRIIB in vivo, an anti-hCD19 Fab is combined with a Fc variant described in Example 1 and the resulting chimeric antibody is compared to an unmodified anti-CD19 antibody with a human IgG1 Fc. These antibodies are added to cultures of human B cells, like the Daudi or Ramos cells, and their ability to stimulate the cells, as measured by release of intracellular calcium is measured. In vivo measurement of the ability of these Fc modified antibodies to arrest B cell activation is measured in a mouse strain deleted for mouse FcRIIB and carrying a transgene for human FcRIIB in its place. These FcRIIB humanized mice are challenged with antigens, such as OVA, and the anti-OVA titer is determined. Treatment of these OVA immunized mice with the anti-CD19 modified Fc is performed and the titer of anti-OVA Ig evaluated. Co-ligation of CD19 with FcRIIB arrests B cell activation with the predicted outcome of reduced OVA specific Ig. Similar experiment can be performed in the collagen induced arthritis model to reduce pathogenic anti-collagen antibodies and thereby reduce the arthritis score of mice treated with the anti-CD 19 Fc modified antibody.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. An amino acid sequence comprising
   a first fragment consisting of amino acids 215-396 of SEQ ID NO: 1, wherein in said fragment, amino acids corresponding to amino acids at positions 215, 326, 359, and 396 of SEQ ID NO: 1 are different from said amino acids present in SEQ ID NO: 1, or
   a second fragment consisting of amino acids 247-354 of SEQ ID NO: 1, wherein in said fragment, amino acids corresponding to amino acids at positions 247, 252, 266, 278, 302, and 354 of SEQ ID NO: 1 are different from said amino acids present in SEQ ID NO: 1, or
   a third fragment consisting of amino acids 211-399 of SEQ ID NO: 1, wherein in said fragment, amino acids corresponding to amino acids at positions 211, 243, 326, and 399 of SEQ ID NO: 1 are different from said amino acids present in SEQ ID NO: 1, or
   a fourth fragment consisting of amino acids 210-378 of SEQ ID NO: 1, wherein in said fragment, amino acids corresponding to amino acids at positions 210, 285, 326, 369, and 378 of SEQ ID NO: 1 are different from said amino acids present in SEQ ID NO: 1.

2. The amino acid sequence of claim 1, wherein:
   the amino acids in said first fragment corresponding to the amino acids at positions 215, 326, 359, and 396 of SEQ ID NO: 1 are isoleucine, glutamate, alanine, and leucine, respectively;
   the amino acids in said second fragment corresponding to the amino acids at positions 247, 252, 266, 278, 302, and 354 of SEQ ID NO: 1 are leucine, leucine, leucine, phenylalanine, glutamate, and threonine, respectively,
   the amino acids in said third fragment corresponding to the amino acids at position 211, 243, 326, and 399 of SEQ ID NO: 1 are alanine, leucine, glutamate, and valine, respectively, and the amino acids in said fourth fragment corresponding to the amino acids at position 210, 285, 326, 369, and 378 of SEQ ID NO: 1 are asparagine, arginine, glutamate, isoleucine, and threonine respectively.

3. An amino acid sequence comprising
a first fragment consisting of amino acids 215-396 of a heavy chain of an IgG, wherein in said first fragment, amino acids corresponding to amino acids at positions 215, 326, 359, and 396 of said heavy chain of the IgG are different from said amino acids present in said heavy chain of the IgG, and wherein the numbering is according to the EU index as in Kabat, or
a second fragment consisting of amino acids 247-354 of a heavy chain of an IgG, wherein in said second fragment, amino acids corresponding to amino acids at positions 247, 252, 266, 278, 302, and 354 of said heavy chain of the IgG are different from said amino acids present in said heavy chain of the IgG, and wherein the numbering is according to the EU index as in Kabat, or
a third fragment consisting of amino acids 211-399 of a heavy chain of an IgG, wherein in said third fragment, amino acids corresponding to amino acids at positions 211, 243, 326, and 399 of said heavy chain of the IgG are different from said amino acids present in said heavy chain of the IgG, and wherein the numbering is according to the EU index as in Kabat, or
a fourth fragment consisting of amino acids 210-378 of a heavy chain of an IgG, wherein in said fourth fragment, amino acids corresponding to amino acids at positions 210, 285, 326, 369, and 378 of said heavy chain of the IgG are different from said amino acids present in said heavy chain of the IgG, and wherein the numbering is according to the EU index as in Kabat.

4. The amino acid sequence of claim 3, wherein:
(1) the amino acids in said first fragment corresponding to the amino acids at positions 215, 326, 359, and 396 are isoleucine, glutamate, alanine, and leucine, respectively, or
(2) the amino acids in said second fragment corresponding to the amino acids at positions 247, 252, 266, 278, 302, and 354 are leucine, leucine, leucine, phenylalanine, glutamate, and threonine, respectively, or
(3) the amino acids in said third fragment corresponding to the amino acids at positions 211, 243, 326, and 399 are alanine, leucine, glutamate, and valine, respectively, or
(4) the amino acids in said fourth fragment corresponding to the amino acids at positions 210, 285, 326, 369, and 378 are asparagine, arginine, glutamate, isoleucine; and threonine, respectively.

5. The amino acid sequence of claim 3, wherein the IgG is IgG1.

6. An antibody variant or immunoadhesin variant comprising a variant of human IgG Fc region, which comprises amino acid substitutions at:
a) positions 215, 326, 359, and 396;
b) positions 247, 252, 266, 278, 302, and 354;
c) positions 211, 243, 326, and 399; or
d) positions 210, 285, 326, 369, and 378,
wherein the numbering of the residues in the IgG Fc region is that of the EU index as in Kabat and
wherein the antibody variant is able to bind an antigen, and the immunoadhesin variant is able to bind a ligand or receptor.

7. The antibody or immunoadhesin variant of claim 6, wherein the substitutions are:
(1) V215I, K326E, T359A, and P396L, or
(2) P247L, M252L, V266L, Y278F, V302E, and S354T, or
(3) V211A, F243L, K326E, and D399V, or
(4) K210N, H285R, K326E, V369I, and A378T.

8. The antibody variant of claim 7,
having a higher affinity to Fc☐RIIB than a control antibody comprising a native Fc sequence, or
having a lower affinity to at least one of FcγRI, FcγRIIA$^{131H}$, FcγRIIA$^{131R}$, FcγIIIA FF, and FcγIIIA FV than a control antibody comprising a native Fc sequence, or
having lower A/I ratio or lower FcγRIIA$^{131H}$/FcγRIIB A/I ratio or lower FcγRIIA$^{131R}$/FcγRIIB A/I ratio than a control antibody comprising a native Fc sequence.

9. The antibody variant of claim 8, wherein said native Fc sequence is characterized by Valine at position 215, Lysine at position 326, Threonine at position 359, Proline at position 396, Proline at position 247, Methionine at position 252, Valine at position 266, Tyrosine at position 278, Valine at position 302, Serine at position 354, Valine at position 211, Phenylalanine at position 243, aspartic acid at position 399, Lysine at position 210, Histidine at position 285, Valine at position 369, and Alanine at position 378, wherein the numbering is according to the EU index as in Kabat.

10. The antibody variant of claim 8, further comprising a light chain, and wherein further, the control antibody further comprises said light chain.

11. The antibody variant of claim 6, which is a monoclonal antibody, a humanized antibody, or a human antibody.

* * * * *